(12) United States Patent
DiMauro et al.

(10) Patent No.: US 8,895,540 B2
(45) Date of Patent: Nov. 25, 2014

(54) LOCAL INTRAOSSEOUS ADMINISTRATION OF BONE FORMING AGENTS AND ANTI-RESORPTIVE AGENTS, AND DEVICES THEREFOR

(75) Inventors: Thomas M. DiMauro, Southboro, MA (US); Mohamed Attawia, Canton, MA (US); Hassan Serhan, South Easton, MA (US); Melissa Grace, Raynham, MA (US); Michael Slivka, Taunton, MA (US); Thomas G. Ferro, Fort Wayne, IN (US); Vivek N. Shenoy, Sunnyvale, CA (US); Alonzo D. Cook, Lakeville, MA (US); Scott Bruder, Sudbury, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 1244 days.

(21) Appl. No.: 10/723,250

(22) Filed: Nov. 26, 2003

(65) Prior Publication Data
US 2005/0112091 A1 May 26, 2005

(51) Int. Cl.
| | | |
|---|---|---|
| A01N 45/00 | (2006.01) | |
| A61K 45/06 | (2006.01) | |
| A61K 33/42 | (2006.01) | |
| A61K 38/39 | (2006.01) | |
| A61K 31/565 | (2006.01) | |
| A61K 39/395 | (2006.01) | |
| A61K 38/18 | (2006.01) | |
| A61K 31/566 | (2006.01) | |
| A61B 17/34 | (2006.01) | |
| A61K 9/00 | (2006.01) | |
| A61M 5/145 | (2006.01) | |
| A61M 5/142 | (2006.01) | |
| A61F 2/30 | (2006.01) | |
| A61F 2/28 | (2006.01) | |

(52) U.S. Cl.
CPC .............. *A61K 33/42* (2013.01); *A61K 45/06* (2013.01); *A61K 38/39* (2013.01); *A61K 31/565* (2013.01); *A61K 39/395* (2013.01); *A61K 38/1875* (2013.01); *A61K 31/566* (2013.01); *A61M 2005/14513* (2013.01); *A61M 5/14276* (2013.01); *A61F 2002/30677* (2013.01); *A61K 38/1825* (2013.01); *A61F 2002/2817* (2013.01); *A61B 17/3472* (2013.01); *A61K 9/0004* (2013.01)
USPC ........................................................ 514/171

(58) Field of Classification Search
USPC ........................................................ 514/171
See application file for complete search history.

(56) References Cited

U.S. PATENT DOCUMENTS

| | | |
|---|---|---|
| 3,678,158 A | 7/1972 | Sussman |
| 4,341,867 A | 7/1982 | Johansen |
| 4,427,649 A | 1/1984 | Dingle et al. |
| 4,435,506 A | 3/1984 | Jackson et al. |
| 4,696,816 A | 9/1987 | Brown |
| 5,095,037 A | 3/1992 | Iwamitsu et al. |
| 5,116,964 A | 5/1992 | Capon et al. |
| 5,194,596 A | 3/1993 | Tischer et al. |
| 5,223,248 A | 6/1993 | McNamara et al. |
| 5,225,538 A | 7/1993 | Capon et al. |
| 5,231,024 A | 7/1993 | Moeller et al. |
| 5,258,371 A | 11/1993 | Golub et al. |
| 5,270,300 A | 12/1993 | Hunziker |
| 5,368,841 A | 11/1994 | Trauner et al. |
| 5,447,851 A | 9/1995 | Beutler et al. |
| 5,510,370 A | 4/1996 | Hock |
| 5,602,156 A | 2/1997 | Kohn et al. |
| 5,656,272 A | 8/1997 | Le et al. |
| 5,656,644 A | 8/1997 | Adams et al. |
| 5,728,396 A | 3/1998 | Peery et al. |
| 5,827,886 A | 10/1998 | Hersh |
| 5,833,984 A | 11/1998 | Eibl et al. |
| 5,842,477 A | 12/1998 | Naughton et al. |
| 5,942,499 A * | 8/1999 | Radomsky .................... 514/54 |
| 5,965,583 A | 10/1999 | Beers et al. |
| 6,015,557 A | 1/2000 | Tobinick et al. |
| 6,049,026 A | 4/2000 | Muschler |
| 6,228,062 B1 | 5/2001 | Howell et al. |
| 6,277,969 B1 | 8/2001 | Le et al. |
| 6,284,471 B1 | 9/2001 | Le et al. |
| 6,294,170 B1 | 9/2001 | Boone et al. |
| 6,300,347 B1 | 10/2001 | Révész |
| 6,340,369 B1 | 1/2002 | Ferree |
| 6,352,557 B1 | 3/2002 | Ferree |
| 6,419,944 B2 | 7/2002 | Tobinick |
| 6,541,477 B2 | 4/2003 | Goehring et al. |
| 6,554,830 B1 | 4/2003 | Chappius |
| 6,590,081 B1 | 7/2003 | Zhang |
| 6,593,310 B1 * | 7/2003 | Cullis-Hill .................... 514/54 |

(Continued)

FOREIGN PATENT DOCUMENTS

| | | |
|---|---|---|
| AU | 2003/263340 A1 | 3/2004 |
| EP | 0 218 868 A2 | 4/1987 |

(Continued)

OTHER PUBLICATIONS

Allali et al. (Ann Rheum Dis 2003; 62: 347-349).*

(Continued)

*Primary Examiner* — Snigdha Maewall

(74) *Attorney, Agent, or Firm* — Hamilton, Brook, Smith & Reynolds, P.C.

(57) ABSTRACT

This invention relates to local administration of a bone-forming agent and at least one anti-resorptive agent to treat osteoporosis and related disorders.

23 Claims, 13 Drawing Sheets

(56) References Cited

U.S. PATENT DOCUMENTS

| | | |
|---|---|---|
| 6,623,472 B1 | 9/2003 | Reinecke et al. |
| 6,713,246 B1 | 3/2004 | Reinecke et al. |
| 6,756,215 B1 | 6/2004 | Wolfraim et al. |
| 7,067,144 B2 | 6/2006 | Demopulos et al. |
| 7,097,834 B1 | 8/2006 | Boyle |
| 7,344,716 B2 | 3/2008 | DiMauro et al. |
| 7,429,378 B2 | 9/2008 | Serhan et al. |
| 7,553,827 B2 | 6/2009 | Attawia et al. |
| 7,727,954 B2 | 6/2010 | McKay |
| 7,741,273 B2 | 6/2010 | McKay |
| 7,799,782 B2 | 9/2010 | Munson et al. |
| 8,067,397 B2 | 11/2011 | Attawia et al. |
| 2001/0006948 A1 | 7/2001 | Kang et al. |
| 2001/0016195 A1 | 8/2001 | Tobinick |
| 2001/0026801 A1 | 10/2001 | Tobinick |
| 2002/0010471 A1 | 1/2002 | Wironen et al. |
| 2002/0019351 A1 | 2/2002 | Ke et al. |
| 2002/0026244 A1* | 2/2002 | Trieu .................. 623/17.16 |
| 2002/0032155 A1 | 3/2002 | Ferree |
| 2002/0082697 A1 | 6/2002 | Damien |
| 2002/0107200 A1 | 8/2002 | Chang et al. |
| 2002/0169162 A1 | 11/2002 | Smith et al. |
| 2003/0007972 A1 | 1/2003 | Tobinick |
| 2003/0008817 A1 | 1/2003 | Sander et al. |
| 2003/0039651 A1 | 2/2003 | Olmarker |
| 2003/0049256 A1 | 3/2003 | Tobinick |
| 2003/0069639 A1 | 4/2003 | Sander et al. |
| 2003/0134792 A1 | 7/2003 | Pike et al. |
| 2003/0207827 A1* | 11/2003 | Boyle et al. .................. 514/44 |
| 2003/0220692 A1 | 11/2003 | Shapiro et al. |
| 2003/0235585 A1 | 12/2003 | Fischkoff et al. |
| 2004/0022864 A1 | 2/2004 | Freyman et al. |
| 2004/0126372 A1 | 7/2004 | Banerjee et al. |
| 2004/0193274 A1 | 9/2004 | Trieu |
| 2004/0228853 A1* | 11/2004 | Serhan et al. ............ 424/94.65 |
| 2004/0229786 A1 | 11/2004 | Attawia et al. |
| 2004/0229878 A1 | 11/2004 | DiMauro et al. |
| 2005/0025765 A1 | 2/2005 | DiMauro et al. |
| 2005/0038001 A1 | 2/2005 | Attawia et al. |
| 2005/0054595 A1* | 3/2005 | Binette et al. .................. 514/44 |
| 2005/0080113 A1 | 4/2005 | Ohkawa et al. |
| 2005/0090501 A1 | 4/2005 | Collis et al. |
| 2005/0100538 A1 | 5/2005 | Mohamed et al. |
| 2005/0112091 A1 | 5/2005 | DiMauro et al. |
| 2005/0282783 A1 | 12/2005 | Bujoli et al. |
| 2006/0085009 A1* | 4/2006 | Truckai et al. .................. 606/94 |
| 2006/0193920 A1 | 8/2006 | Bosch et al. |
| 2006/0210552 A1 | 9/2006 | Demopulos et al. |
| 2007/0237777 A1 | 10/2007 | DiMauro et al. |
| 2007/0243228 A1 | 10/2007 | McKay |
| 2008/0213261 A1 | 9/2008 | DiMauro et al. |
| 2009/0068270 A1 | 3/2009 | Attawia et al. |
| 2009/0155364 A1 | 6/2009 | Serhan et al. |
| 2009/0162351 A1 | 6/2009 | Brown et al. |
| 2009/0162376 A1 | 6/2009 | Brown et al. |
| 2009/0175943 A1 | 7/2009 | Attawia et al. |
| 2009/0324558 A1 | 12/2009 | Attawia et al. |
| 2010/0158800 A1 | 6/2010 | Mckay |
| 2010/0189757 A1 | 7/2010 | Mckay |

FOREIGN PATENT DOCUMENTS

| | | |
|---|---|---|
| EP | 0 288 088 B1 | 10/1988 |
| EP | 0 438 234 A1 | 7/1991 |
| EP | 0 950 417 A2 | 2/1999 |
| EP | 1 133 995 A2 | 9/2001 |
| EP | 1 153 607 A2 | 11/2001 |
| EP | 1 464 307 A1 | 10/2004 |
| WO | WO 91/02078 | 2/1991 |
| WO | WO 92/07076 | 4/1992 |
| WO | WO 92/16553 A1 | 10/1992 |
| WO | WO 93/16099 | 8/1993 |
| WO | WO 97/28828 A1 | 8/1997 |
| WO | WO 98/24477 A1 | 6/1998 |
| WO | WO 99/45923 | 9/1999 |
| WO | WO 00/18409 | 4/2000 |
| WO | WO 00/50079 | 8/2000 |
| WO | WO 01/85179 A2 | 11/2001 |
| WO | WO 02/057240 A1 | 7/2002 |
| WO | WO 02/100387 A1 | 12/2002 |
| WO | WO 03/000190 A2 | 1/2003 |
| WO | WO 2004/022078 A1 | 3/2004 |
| WO | WO 2004/039248 | 5/2004 |
| WO | WO 2005/000283 A2 | 1/2005 |
| WO | WO 2005/011689 A2 | 2/2005 |
| WO | WO 2005/049055 A1 | 6/2005 |
| WO | WO 2005/053795 A2 | 6/2005 |
| WO | WO 2005/110276 A1 | 11/2005 |
| WO | WO 2006/031376 A2 | 3/2006 |

OTHER PUBLICATIONS

Bertolini et al. ( Nature vol. 319 Feb. 6, 1986).*
Brandt et al., (Arthritis and Rheumatism vol. 43. No. 6, Jun. 2000, 1346-1352 ).*
( Kitazawa et al. J. Clin. Invest. vol. 94, Dec. 1994, 2397-2406).*
Weitzmann et al. (J. Clin. Invest. 110:1643-1650 (2002), Increased production of IL-7 uncouples bone formation from bone resorption during estrogen deficiency).*
Pacifici, R., "Editorial: Cytokines, Estrogen, and Postmenopausal Osteoporosis-The Second Decade," *Endocrinology*, 139(6):2659-2661 (1998).
Allali, F. et al., "Increase in Bone Mineral Density of Patients with Spondyloarthropathy Treated with Anti-Tumour Necrosis Factor α," *Ann. Rheum. Dis.*, 62:347-349 (2003).
Tobinick, E.L., "Targeted Etanercept for Treatment-Refractory Pain Due to Bone Metastasis: Two Case Reports," *Clin. Ther.*, 25(8):2279-2288 (2003).
Biskobing, D.M., "Novel Therapies for Osteoporosis," *Expert Opinion Invest. Drugs*, 12(4):611-621 (2003).
Vahle, J.L. et al., "Skeletal Changes in Rats Given Daily Subcutaneous Injections of Recombinant Human Parathyroid Hormone (1-34) for 2 Years and Relevance to Human Safety," *Toxicol. Pathol.*, 30(3):312-321 (2002).
Rodan, G.A. et al., "Therapeutic Approaches to Bone Diseases," *Science*, 289:1508-1514 (2000).
Nakamura, K. et al., "Local Application of Basic Fibroblast Growth Factor into the Bone Increases Bone Mass at the Applied Site in Rabbits," *Arch. Orthop. Trauma Surg.*, 115(6):344-346 (1996).
Lane, N.E. et al., "Basic Fibroblast Growth Factor Forms New Trabeculae that Physically Connect with Pre-Existing Trabeculae, and This New Bone is Maintained with an Anti-Resorptive Agent and Enhanced with an Anabolic Agent in an Osteopenic Rat Model," *Osteoporos. Int.*, 14:374-382 (2003).
Goodman, S. et al., "Effects of Local Infusion of TGFβ on Bone Ingrowth in Rabbit Chambers," *J. Biomed. Mat. Res. (Appl Biomater)*, 53:475-479 (2000).
Pederson, A.W. et al., "Thermal Assembly of a Biomimetic Mineral/Collagen Composite," *Biomaterials*, 24:4881-4890 (2003).
Kimble, R.B. et al., "Estrogen Deficiency Increases the Ability of Stromal Cells to Support Murine Osteoclastogenesis Via an InterLeukin-1 and Tumor Necrosis Factor-Mediated Stimulation of Macrophage Colony-Stimulating Factor Production," *J. Biol. Chem.* 271(46):28890-28897 (1996).
Kimble, R.B. et al., "The Functional Block of TNF but Not of IL-6 Prevents Bone Loss in Ovariectomized Mice," *J. Bone Min. Res.*, 12(6):935-941 (1997).
Lee, J.C. et al., "Inhibition of p38 MAP Kinase as a Therapeutic Strategy," *Immunopharmacology*, 47:185-201 (2000).
Boehm, J. and Adams, J., "New Inhibitors of p38 Kinase," *Exp. Opin. Ther. Patents*, 10(1):25-37 (2000).
Kozbor, D. and Roder J., "The Production of Monoclonal Antibodies from Human Lymphocytes," *Immunol. Today*, 4:72-79 (1983).
"Hydrogels", *Encyclopedia of Polymer Science and Technology*, (Wiley and Sons, 2003).
Müller, R., "Determination of Affinity and Specificity of Anti-Hapten Antibodies by Competitive Radioimmunoassay," *Meth. Enzymol.*, 92:589-601 (1983).

(56) References Cited

OTHER PUBLICATIONS

Möller, A. et al., "Monoclonal Antibodies to Human Tumor Necrosis Factor α: In Vitro and in Vivo Application," *Cytokine*, 2(3):162-169 (1990).
Meager, A. et al., "Preparation and Characterization of Monoclonal Antibodies Directed Against Antigenic Determinants of Recombinant Human Tumour Necrosis Factor (rTNF)," *Hybridoma*, 6(3):305-311 (1987).
Fendly, B.M. et al., "Murine Monoclonal Antibodies Defining Neutralizing Epitopes on Tumor Necrosis Factor," *Hybridoma*, 6(4):359-370 (1987).
Bringman, T.S. et al., "Monoclonal Antibodies to Human Tumor Necrosis Factors Alpha and Beta: Application for Affinity Purification, Immunoassays, and as Structural Probes," *Hybridoma*, 6(5):489-507 (1987).
Hirai, M. et al., "Production and Characterization of Monoclonal Antibodies to Human Tumor Necrosis Factor," *J. Immunol. Meth.*, 96:57-62 (1987).
Schall, T.J. et al., "Molecular Cloning and Expression of a Receptor for Human Tumor Necrosis Factor," *Cell*, 61:361-370 (1990).
Loetscher, H. et al., "Molecular Cloning and Expression of the Human 55 kd Tumor Necrosis Factor Receptor," *Cell*, 61:351-359 (1990).
Corcoran, A.E. et al., "Characterization of Ligand Binding by the Human p55 Tumour-Necrosis-Factor Receptor," *Eur. J. Biochem.*, 223:831-840 (1994).
Engelmann, H. et al., "Two Tumor Necrosis Factor-Binding Proteins Purified from Human Urine," *J. Biol. Chem.*, 265(3):1531-1536 (1990).
Lesslauer, W. et al., "Recombinant Soluble Tumor Necrosis Factor Receptor Proteins Protect Mice From Lipopolysaccharide-Induced Lethality," *Eur. J. Immunol.*, 21:2883-2886 (1991).
Ashkenazi, A. et al., "Protection Against Endotoxic Shock by a Tumor Necrosis Factor Receptor Immunoadhesin," *Proc. Natl. Acad. Sci. USA*, 88:10535-10539 (1991).
Peppel, K. et al., "A Tumor Necrosis Factor (TNF) Receptor-IgG Heavy Chain Chimeric Protein as a Bivalent Antagonist of TNF Activity," *J. Exp. Med.*, 174:1483-1489 (1991).
Kolls, J. et al., "Prolonged and Effective Blockade of Tumor Necrosis Factor Activity Through Adenovirus-Mediated Gene Transfer," *Proc. Natl. Acad. Sci. USA*, 91:215-219 (1994).
Butler, D.M. et al. "TNF Receptor Fusion Proteins are Effective Inhibitors of TNF-Mediated Cytotoxicity on Human KYM-1D4 Rhabdomyosarcoma Cells," *Cytokine*, 6(6):616-623 (1994).
Baker, D. et al., "Control of Established Experimental Allergic Encephalomyelitis by Inhibition of Tumor Necrosis Factor (TNF) Activity Within the Central Nervous System Using Monoclonal Antibodies and TNF Receptor-Immunoglobulin Fusion Proteins," *Eur. J. Immunol.*, 24:2040-2048 (1994).
Capon, D.J. et al., "Designing CD4 Immunoadhesins for AIDS Therapy," *Nature*, 337:525-531 (1989).
Cirillo, P.F. et al., "The Non-Diaryl Heterocycle Classes of p38 MAP Kinase Inhibitors," *Current Topics in Medicinal Chemistry*, 2:1021-1035 (2002).
Zhang, C., "Mitogen-activated Protein (MAP) Kinase Regulates Production of Tumor Necrosis Factor-α and Release of Arachidonic Acid in Mast Cells," *J. Biol. Chem.*, 272(20):13397-13402 (1997).
Pargellis, C., "Inhibition of p38 MAP Kinase by Utilizing a Novel Allosteric Binding Site," *Nature Structural Biology*, 9(4):268-272 (2002).
Chae, H.J., "The p38 Mitogen-Activated Protein Kinase Pathway Regulates Interleukin-6 Synthesis in Response to Tumor Necrosis Factor in Osteoblasts," *Bone*, 28(1):45-53 (2001).
DeSantis, A. and Buchman, A., "Current and Emerging Therapies in Osteoporosis," *Expert Opin. Pharmacother.*, 3(7):835-843 (2002).
Nakamura, K. et al., "Stimulation of Endosteal Bone Formation by Local Intraosseous Application of Basic Fibroblast Growth Factor in Rats," *Rev. Rhum. [Engl. Ed.]*, 64(2):101-105 (1997).

Ezra, A., and Golomb, G., "Administration Routes and Delivery Systems of Bisphosphonates for the Treatment of Bone Resorption," *Adv. Drug Del. Rev.*, 42:175-195 (2000).
Crandall, C., "Combination Treatment of Osteoporosis: A Clinical Review," *J. of Women's Health & Gender-Based Medicine*, 11(3):211-224 (2002).
Yaffe, A. et al., "Combined Local Application of Tetracycline and Bisphosphonate Reduces Alveolar Bone Resporption in Rats," *J. Periodontol*, 74:1038-1042 (2003).
Abstracts of the North American Spine Society 17 Annual Meeting, Montreal, Canada, Oct. 29 through Nov. 2, 2002, The Spine Journal 2(5 Suppl):49S-50S (2002).
Ahn, N. U., et al., "Effect of Nutrient Concentration and OP-1 on the Metabolism of Intervertebral Disc: In Vitro Organ Culture Study," 28, Abstracts of the 30th Annual Meeting of the International Society for the Study of the Lumbar Spine, Vancouver, Canada (May 2003).
Alini, M., et al., "A Biological Approach in Treating Disc Degeneration: Not for Today, but Maybe for Tomorrow," *European Spine Journal*, 11(Suppl 2):S215-S220 (2002).
Andonopoulos, A. P., et al., "Intra-articular Anti-Tumor Necrosis Factor α Antibody in Recalcitrant Arthritis of Behçet's Disease," *Clinical and Experimental Rheumatology* 21(4 Suppl 30):S-57-S58 (Jul.-Aug. 2003).
Aoki, Y., et al., "Local Application of Disc-Related Cytokines on Spinal Nerve Roots," *Spine* 27(15): 1614-1617 (2002).
Arai, I., et al., "Pretreatment with Loxoprofen Sodium, 6-OHDA or Anti TNF-Alpha Antibody Reduce Fos-Like Immunoreactivity in Rat Experimental Lumber Disc Herniation," *111, Abstracts of the 30th Annual Meeting of the International Society for the Study of the Lumbar Spine*, Vancouver, Canada (May 2003).
Ariga, K., et al., "Mechanical Stress-Induced Apoptosis of Endplate Chondrocytes in Organ-Cultured Mouse Intervertebral Discs," *Spine*, 28(14):1528-1533 (2003).
Bokarewa, M., and Tarkowski, A., "Local Infusion of Infliximab for the Treatment of Acute Joint Inflammation," *Ann. Rheum. Dis.*, downloaded from ard.bmjjournals.com on Nov. 30, 2005, www.annrheumdis.com 62:783-784 (2003).
Braun, J. and Sieper, J., "Overview of the Use of the Anti-TNF Agent Infliximab in Chronic Inflammatory Diseases," *Expert Opin. Biol. Ther.* 3(1):141-168 (2003).
Braun, J., et al., "Anti-Tumour Necrosis Factor α Therapy for Ankylosing Spondylitis: International Experience," *Ann. Rheum. Dis.*, 61(Supp. III):iii51-iii60 (2002).
Bringman, T.S., et al., "Monoclonal Antibodies to Human Tumor Necrosis Factors Alpha and Beta: Application for Affinity Purification, Immunoassays, and as Structural Probes," *Hybridoma*, 6(5):489-507 (1987).
Brown, K., et al., "Gelatin/Chondroitin 6-Sulfate Microspheres for the Delivery of Therapeutic Proteins to the Joint," *Arthritis. & Rheum.*, 41(12):2185-2195 (1998).
Burke, J. G., et al., "Human Nucleus Pulposus Secretes Transforming Growth Factor Beta-1 and Basic Fibroblast Growth Factor," *189, Abstracts of the 30th Annual Meeting of the International Society for the Study of the Lumbar Spine*, Vancouver, Canada (May 2003).
Burke, J.G., et al., "Intervertebral Discs Which Cause Low Back Pain Secrete High Levels of Proinflammatory Mediators," *J. Bone Joint Surg.* [Br], 84-B, 196-201 (2002).
Cardone, D.A., and Tallia, A.F., "Diagnostic and Therapeutic Injection of the Hip and Knee," *Am. Fam. Physician*, 67(10):2147-2152 (2003).
Connolly, J., et al., "Development of an Osteogenic Bone-Marrow Preparation," *J. of Bone and Joint Surgery, Inc.*, 71-A (5):684-691 (1989).
Conti, F., et al., "Successful Treatment With Intraarticular Infliximab for Resistant Knee Monarthritis in a Patient With Spondylarthropathy," *Arthritis & Rheumatism*, 52(4):1224-1226 (2005).
Cornefjord, M., et al., "Cerebrospinal Fluid Biomarkers in Experimental Spinal Nerve Root Injury," *38, Abstracts of the 30th Annual Meeting of the International Society for the Study of the Lumbar Spine*, Vancouver, Canada (May 2003).

(56) References Cited

OTHER PUBLICATIONS

Dayer, J.M., "The Pivotal Role of Interleukin-1 in the Clinical Manifestations of Rheumatoid Arthritis," *Rheumatology, Oxford University Press*, London, GB, 42(Suppl 2):ii3-ii10 (2003).
Diwan, A.D., et al., "Current Concepts in Intervertebral Disk Restoration," *Tissue Engineering in Orthopedic Surgery*, 31(3):453-464 (2000).
Edwards, S. L., et al., "Radiographic Assessment of Posterolateral Spine Fusion With and Without Platelet Rich Plasma," *117, Abstracts of the 30th Annual Meeting of the International Society for the Study of the Lumbar Spine*, Vancouver, Canada (May 2003).
Eustice, Carol & Richard, "What is Viscosupplementation?" http://arthritis.com/od/kneetreatments/g/viscosupplements_p.htm, Dec. 9, 2005.
Frain, J., et al., "Use of cDNA Microarrays to Investigate Cytokine Expression in Intervertebral Disc Degeneration," *126, Abstracts of the 30th Annual Meeting of the International Society for the Study of the Lumbar Spine*, Vancouver, Canada (May 2003).
Gabay, C., "IL-1 Trap," *Curr. Opin. Invest. Drugs, Curr. Drugs*, London, GB, 4(5):593-597 (2003).
Ganey, T.M., and Meisel, H.J., "A Potential Role for Cell-Based Therapeutics in the Treatment of Intervertebral Disc Herniation," *Eur. Spine J.*, 11 (Suppl. 2): S206-S214 (2002).
Gordon, J.L., et al., "Metalloproteinase Inhibitors as Therapeutics," *Clin. Exp. Rheumatol.*, 11(Suppl. 8): S91-S94 (1993).
Goupille, P., et al., "Matrix Metalloproteinases: The Clue to Intervertebral Disc Degeneration?," *Spine*, 23(14): 1612-1626 (1998).
Kawakami, M., et al., "Role of IL-8, MCP-1 and PH in Neuropathic Pain Enhanced by Degenerative Nucleus Pulposus," *127, Abstracts of the 30th Annual Meeting of the International Society for the Study of the Lumbar Spine*, Vancouver, Canada (May 2003).
Hunter, C. J., et al., "Functional Behavior of Notochordal Cell Clusters in the Canine Nucleus Pulposus: Cell Communication and Survival," *70, Abstracts of the 30th Annual Meeting of the International Society for the Study of the Lumbar Spine*, Vancouver, Canada (May 2003).
Igarashi, A., et al., "Inflammatory Cytokines Release From Facet Joint Tissue in Degenerative Lumbar Disorders," *262, Abstracts of the 30th Annual Meeting of the International Society for the Study of the Lumbar Spine*, Vancouver, Canada (May 2003).
Imai, Y., et al., "Effect of Recombinant Human Osteogenic Protein-1 on Extracellular Matrix Metabolism by Human Annulus Fibrosus and Nucleus Pulposus Cells," *205, Abstracts of the 30th Annual Meeting of the International Society for the Study of the Lumbar Spine*, Vancouver, Canada (May 2003).
Imai, Y., et al., "The Quantification of Cytokine-Induced Matrix Catabolism in Tissue Engeneered Intervertebral Discs," *67, Abstracts of the 30th Annual Meeting of the International Society for the Study of the Lumbar Spine*, Vancouver, Canada (May 2003).
Inui, Y., et al., "Fas-Ligand Expression on Nucleus Pulposus Cells Begins in Developing Embryo," *42, Abstracts of the 30th Annual Meeting of the International Society for the Study of the Lumbar Spine*, Vancouver, Canada (May 2003).
Johnson, W.H., et al., "Collagenase Inhibitors: Their Design and Potential Therapeutic Use," *J. Enzyme Inhib.*, 2:1-22 (1987).
Karppinen, J., et al., "Tumor Necrosis Factor-α Monoclonal Antibody, Infliximab, Used to Manage Severe Sciatica," *Spine*, 28(8):750-754 (2003).
Kato, H., et al., "The Effect of IL-1 on the Rabbit Intervertebral Disc in Vivo," *199, Abstracts of the 30th Annual Meeting of the International Society for the Study of the Lumbar Spine*, Vancouver, Canada (May 2003).
Kawakami, M., et al., "Possible Mechanism of Painful Radiculopathy in Lumbar Disc Herniation," *Clin. Orthop.*, 351:241-251(1998).
Koch, H., et al., "Spontaneous Secretion of Interleukin 1 Receptor Antagonist (IL-1Ra) by Cells Isolated From Herniated Lumbar Discal Tissue After Discectomy," *Cytokine*, 10(9):703-705 (1998).

Ohtori, S., et al., "TNF-αDeficient Mice Have Fewer Macrophages in Injured Nerve and Reduced Glial Activation in DRG and Spinal Cord," *250, Abstracts of the 30th Annual Meeting of the International Society for the Study of the Lumbar Spine*, Vancouver, Canada (May 2003).
Korhonen, T., et al., "Efficacy of Infliximab for Disc Herniation-Induced Sciatica One-Year Follow-Up," *14, Abstracts of the 30th Annual Meeting of the International Society for the Study of the Lumbar Spine*, Vancouver, Canada (May 2003).
Kwon, U-H., et al., "Dexamethsone Stimulates Cellular Proliferation While Downregulates Matrix Synthesis in Intervertebral Disc Cells," *29, Abstracts of the 30th Annual Meeting of the International Society for the Study of the Lumbar Spine*, Vancouver, Canada (May 2003).
Lane, N. E. et al., "Basic Fibroblast Growth Factor Forms New Trabeculae That Physically Connect With Pre-Existing Trabeculae, and This New Bone is Maintained With an Anti-Resorptive Agent and Enhanced With an Anabolic Agent in an Osteopenic Rat Model," *Osteoporos. Int.*, 14:374-382 (2003).
LaVan, D. A., et al., "Small-scale Systems for in vivo Drug Delivery," *Nature, Biotechnology*, 21(10):1184-1191 (2003).
Lee, C. S., et al., "A Single Period of Hyperphysiologic Stretch Induces IL-6, TGF-beta and Cell Proliferation in Anulus Fibrosus Cells," *215, Abstracts of the 30th Annual Meeting of the International Society for the Study of the Lumbar Spine*, Vancouver, Canada (May 2003).
Lehman, T. J. A., et al., "Thalidomide Therapy for Recalcitrant Systemic Onset Juvenile Rheumatoid Arthritis," *J. Pediatrics*, 140(1):125-127 (2002).
Le Maitre, C. L., et al., "Expression of the IL-1 Family in Human Intervertebral Disc," *217, Abstracts of the 30th Annual Meeting of the International Society for the Study of the Lumbar Spine*, Vancouver, Canada (May 2003).
Le Maitre, C. L., et al., "Response of Human Intervertebral Disc Cells to IL-1," *216, Abstracts of the 30th Annual Meeting of the International Society for the Study of the Lumbar Spine*, Vancouver, Canada (May 2003).
Le Visage, C., et al., "Interaction of Human Mesenchymal Stem Cells with Disc Cells: Changes in Biosynthesis of Extracellular Matrix," *25, Abstracts of the 30th Annual Meeting of the International Society for the Study of the Lumbar Spine*, Vancouver, Canada (May 2003).
Li, J., et al., "The Effects of Bone Morphogenetic Protein 2 (BMP-2) and Cartilage-Derived Morphogentic Protein 2 (CDMP-2) on Aggrecan Gene Expression in Chondrocytes," *30, Abstracts of the 30th Annual Meeting of the International Society for the Study of the Lumbar Spine*, Vancouver, Canada (May 2003).
Liang, C.-M., et al., "Production and Characterization of Monoclonal Antibodies Against Recombinant Human Tumor Necrosis Factor/Cachectin," *Biochem. Biophys. Res. Comm.* 137 (2):847-854 (1986).
Lotz, J. C., et al., "Cytokines in Normal, Degenerated, and Nucleoplasty-Treated Porcine Discs," *157, Abstracts of the 30th Annual Meeting of the International Society for the Study of the Lumbar Spine*, Vancouver, Canada (May 2003).
Maeda, S. and Kokubun, S., "Changes With Age in Proteoglycan Synthesis in Cells Cultured In Vitro From the Inner and Outer Rabbit Annulus Fibrosus," *Spine*, 25(2):166-169 (2000).
Meijer, H., et al., "The Production of Anti-Inflammatory Cytokines in Whole Blood by Physico-Chemical Induction," *Inflamm. Res.*, 52: 404-407 (2003).
Miyamoto, H., et al., "The Effect of Mechanical Stress on the Production of Inflammatory Agents by Disc Cells," *110, Abstracts of the 30th Annual Meeting of the International Society for the Study of the Lumbar Spine*, Vancouver, Canada (May 2003).
Sakai, D., et al., "Autologous Transplantation of Mesenchymal Stem Cells for Disc Repair," *24, Abstracts of the 30th Annual Meeting of the International Society for the Study of the Lumbar Spine*, Vancouver, Canada (May 2003).
Molloy, T., et al., "The Roles of Growth Factors in Tendon and Ligament Healing," *Sports Med.*, 33(5): pp. 381-394 (2003).
Nikas, S. N., et al., "Treatment of Resistant Rheumatoid Arthritis by Intra-Articular Infliximab Injections: A Pilot Study," *Ann. Rheum. Dis.*, downloaded from ard.bmjjournals.com on Nov. 2, 2005, www.annrheumdis.com 63: 102-103 (2004).

(56) References Cited

OTHER PUBLICATIONS

Ohtori, S., et al., "TNF-α and TNF-α Receptor 1 Upregulation in GLIA and Neurons After Nerve Injury. Studies in Murine DRG and Spinal Cord," *13, Abstracts of the 30th Annual Meeting of the International Society for the Study of the Lumbar Spine*, Vancouver, Canada (May 2003).

Olmarker, K. and Rydevik, B., "Selective Inhibition of Tumor Necrosis Factor-α Prevents Nucleus Pulposus-Induced Thrombus Formation, Intraneural Edema, and Reduction of Nerve Conduction Velocity," *Spine*, 26(8):863-869 (2001).

Richardson, S., et al., "Human Bone Marrow Mesenchymal Stromal Cells as a Source of Chondrocytes for Treatment of Intervertebral Disc Degeneration," *27, Abstracts of the 30th Annual Meeting of the International Society for the Study of the Lumbar Spine*, Vancouver, Canada (May 2003).

Sakai, D., et al., "Transplantation of Mesenchymal Stem Cells Embedded in Atelocollagen® Gel to the Intervertebral Disc: A Potential Therapeutic Model for Disc Degeneration," *Biomaterials*, 24:3531-3541 (2003).

Schatteman, L., et al., "Treatment of Refractory Inflammatory Monoarthritis in Ankylosing Spondylitis by Intraarticular Injection of Infliximab," *J. Of Rheum.*, 33:1:82-85 (2006).

Sobajima, S., et al., "Stem Cell Therapy for Degenerative Disc Disease: An In-Vitro Feasibility Study," *43, Abstracts of the 30th Annual Meeting of the International Society for the Study of the Lumbar Spine*, Vancouver, Canada (May 2003).

Stern, S., et al., "Human Intervertebral Disc Cell Culture for Disc Disorders," *Clin. Orthop.*, 919:238-244 (2004).

Takada, T., et al., "IL-6 Production was Upregulated by Interaction Between Disc Tissue and Macrophages," *41, Abstracts of the 30th Annual Meeting of the International Society for the Study of the Lumbar Spine*, Vancouver, Canada (May 2003).

Takegami, K. et al., "Osteogenic Protein-1 Enhances Matrix Replenishment by Intervertebral Disc Cells Previously Exposed to Interleukin-1," *Spine*, 27(12):1318-1325 (2002).

Tobinick, E.L., "Targeted Etanercept for Discogenic Neck Pain: Uncontrolled, Open-Label Results in Two Adults," *Clin. Ther.*, 25(4):1211-1218 (2003).

Tobinick, E.L. and Davoodifar, S., "Perispinal TNF-alpha Inhibition for Discogenic Pain," *Swiss Med. Weekly*, 133:170-177 (2003).

Tsuji, T., et al., "Age-Related Changes in M-RNA Expression of Various Regulatory Factors in Rabbit Intervertebral Disc," *81, Abstracts of the 30th Annual Meeting of the International Society for the Study of the Lumbar Spine*, Vancouver, Canada (May 2003).

Weiler, C., et al., "Expression of TNF-α in Autopsy and Biopsy Specimens of Intervertebral Discs of Various Age and Degeneration," *233, Abstracts of the 30th Annual Meeting of the International Society for the Study of the Lumbar Spine*, Vancouver, Canada (May 2003).

Wittenberg, R.H., et al., "In Vitro Release of Prostaglandins and Leukotrienes From Synovial Tissue, Cartilage, and Bone in Degenerative Joint Diseases," *Arthritis Rheum.*, 36(10):1444-1450 (1993).

Xie, X., et al., "Treatment of Spondylodiscitis Intravenous Versus Percutaneous Intradiscal Applications of Antibiotics: An Experimental Study in Rabbits," *120, Abstracts of the 30th Annual Meeting of the International Society for the Study of the Lumbar Spine*, Vancouver, Canada (May 2003).

Yabuki, S., et al., "Prevention of Compartment Syndrome in Dorsal Root Ganglia Caused by Exposure to Nucleus Pulposus," *Spine*, 26(8):870-875 (2001).

Yoon, S. T., et al., "LMP-1 Upregulates Proteoglycan Synthesis in Intervertebral Disc Cells Through a BMP Mediated Process," *31, Abstracts of the 30th Annual Meeting of the International Society for the Study of the Lumbar Spine*, Vancouver, Canada (May 2003).

Hawks, D., "Alternative Medicine: Musculoskeletal System," *Clin. Tech. Small Anim. Pract.*, 17(1):41-49 (2002).

Khot, A. et al., "The Use of Intradiscal Steroid Therapy for Lumbar Spinal Discogenic Pain—A Randomized Controlled Trial," *Spine*, 29(8):833-837 (2004).

Földes, I. et al., "Trace Elements in Tissues of Normal and Vitamin $D_2$-Treated Rats," *ACTA Biol. Acad. Sci. Hung.*, 26(3-4):141-150 (1975).

Benjamin, L.E. et al., "A Plasticity Window for Blood Vessel Remodelling is Defined by Pericyte Coverage of the Preformed Endothelial Network and is Regulated by PDGF-B and VEGF," *Development*, 125:1591-1598 (1998).

Vukicevic, S. et al., "Induction of Nephrogenic Mesenchyme by Osteogenic Protein 1 (Bone Morphogenetic Protein 7)," *Proc. Natl. Acad. Sci.*, 93:9021-9026 (1996).

Moreira, A.L. et al., "Thalidomide Exerts Its Inhibitory Action on Tumor Necrosis Factor α by Enhancing mRNA Degradation," *J. Exp. Med.*, 177:1675-1680 (1993).

CN 1 647 808 A (Zhou C) Aug. 3, 2005 (abstract) World Patents Index [online]. London, GB: Derwent Publications, Ltd., Week 200621, Class B04, Accession No. 2006-194507.

CN 1 569 039 A (Niu X) Jan. 26, 2001 (abstract) World Patents Index [online]. London, GB: Derwent Publications, Ltd., Week 200577, Class B04, Accession No. 2005-749289.

Shiel, W.C., Ankylosing Spondylitis, MedicineNet.com [online], Sep. 2005 [retrieved on Jun. 20, 2006]. Retrieved from the Internet <URL: http://www.medicinenet.com/script/main/art.asp?articlekey=274&pf=3&page=2>.

Sampaio, E.P. et al, "Thalidomide Selectively Inhibits Tumor Necrosis Factor α Production by Stimulated Human Monocytes," *J. Exp. Med.*, 173:699-703 (1991).

Muller, G.W. et al., "Amino-Substituted Thalidomide Analogs: Potent Inhibitors of TNF-α Production," *Bioorg. Med. Chem. Lett.*, 9:1625-1630 (1999).

Teo, S.K., "Properties of Thalidomide and its Analogues: Implications for Anticancer Therapy," *AAPS Journal* 7(1):E14-E19 (2005).

Crevensten, G. et al., "Intervertebral Disc Cell Therapy for Regeneration: Mesenchymal Stem Cell Implantation in Rat Intervertebral Discs," *Ann. Biomed. Eng.*, 32(3):430-434 (2004).

Tracey, K.J. and Cerami, A., "Tumor Necrosis Factor in Metabolism of Disease: Hormonal Actions Versus Local Tissue Effects," *Nouv. Rev. Fr. Hematol.*, 34 *Suppl*:S37-42 (1992) (abstract).

Haro, H. et al., "Matrix Metalloproteinase-7-Dependent Release of Tumor Necrosis Factor-α in a Model of Herniated Disc Resorption," *J. Clin. Invest.*, 105(2):143-150 (2000).

Ohno, K. and Oshita, S., "Transdiscal Lumbar Sympathetic Block: A New Technique for a Chemical Sympathectomy," *Anesth. Analg.*, 85:1312-1316 (1997).

Tanny, G.B. et al., "Improved Filtration Technique for Concentrating and Harvesting Bacteria," *Appl. Environ. Microbiol.*, 40(2):269-273 (1980).

Raucci, A. et al., "Activation of the ERK1/2 and p38 Mitogen-Activated Protein Kinase Pathways Mediates Fibroblast Growth Factor-Induced Growth Arrest of Chondrocytes," *J. Biol. Chem.*, 279(3):1747-1756 (2004).

Marriott, J.B. et al., "CC-3052: A Water-Soluble Analog of Thalidomide and Potent Inhibitor of Activation-Induced TNF-α Production," *J. Immunol.*, 161:4236-4243 (1998).

Abbas-Ghaleb, K. et al, "Preconcentration of Selenium Compounds on a Porous Graphitic Carbon Column In View of HPLC-ICP-AES Speciation Analysis," *Anal. Bioanal. Chem.*, 377:1026-1031 (2003).

Awasthi, Y.C. et al., "Purification and Properties of Human Erythrocyte Glutathione Peroxidase," *J. Biol. Chem.*, 250(13):5144-5149 (1975).

Biemond, P. et al., "Protective Factors Against Oxygen Free Radicals and Hydrogen Peroxide in Rheumatoid Arthritis Synovial Fluid," *Arthritis Rheum.*, 27(7):760-765 (1984).

Ceponis, A. et al. "Effects of Low-Dose, Noncytotoxic, Intraarticular Liposomal Clodronate on Development of Erosions and Proteoglycan Loss in Established Antigen-Induced Arthritis in Rabbits," *Arthritis and Rheum.*, 44(8): 1908-1916 (2001).

Chan, J.M.K. et al., "Intraarticular Gene Transfer of TNFR:Fc Suppresses Experimental Arthritis with Reduced Systemic Distribution of the Gene Product," *Mol. Ther.*, 6(6): 727-736 (2002).

Desai, S. et al., "Coated Microwell Plate-Based Affinity Purification of Antigens," *Anal. Biochem.*, 328: 162-165 (2004).

(56) References Cited

OTHER PUBLICATIONS

Guillen, C. et al., "The Effects of Local Administration of Lactoferrin on Inflammation in Murine Autoimmune and Infectious Arthritis," *Arthritis Rheum.*, 43(9):2073-2080 (2000).

Hayashida, K. et al., "Lactoferrin Enhances Peripheral Opioid-Mediated Antinociception via Nitric Oxide in Rats," *Eur. J. Pharmacol.*, 484:175-181 (2004).

Hayashida, K. et al., "Oral Administration of Lactoferrin Inhibits Inflammation and Nociception in Rat Adjuvant-Induced Arthritis," *J. Vet. Med. Sci.*, 66(2):149-154(2004).

Kamanh, A. et al., "Plasma Lipid Peroxidation and Antioxidant Levels in Patients with Rheumatoid Arthritis," *Cell Biochem. Funct.*, 22:53-57 (2004).

Kilic, B.A. et al., "Effects of Intra-Articular Vitamin E and Corticosteroid Injection in Experimental Hemarthrosis in Rabbits," *Pediatr. Hematol. Oncol.*, 15(4):339-346 (1998).

Kim, S.H. et al. "Ex Vivo Gene Delivery of IL-1Ra and Soluble TNF Receptor Confers a Distal Synergistic Therapeutic Effect in Antigen-Induced Arthritis," *Mol. Ther.*, 6(5): 591-600 (2002).

Kurz, B. et al., "Dietary Vitamins and Selenium Diminish the Development of Mechanically Induced Osteoarthritis and Increase the Expression of Antioxidative Enzymes in the Knee Joint of STR/1N Mice," *Osteoarthritis Cartilage*, 10:119-126 (2002).

Lubberts, E. et al., "Intra-Articular IL-10 Gene Transfer Regulates the Expression of Collagen-Induced Arthritis (CIA) in the Knee and Ipsilateral Paw," *Clin. Exp. Immunol.*, 120:375-383 (2000).

Maddipati, K.R. and Marnett, L.J., "Characterization of the Major Hydroperoxide-Reducing Activity of Human Plasma," *J. Biol. Chem.*, 262(36):17398-17403 (1987).

Martinez, J.I.R., et al, "Blood Platelet Glutathione Peroxidase: Some Properties and Partial Purification," *Thromb. Res.*, 19:73-83 (1980).

Niccoli, L. et al., "Intraarticular Injection of Infliximab in Relapsing Knee Effusion in Psoriatic Arthritis: A Pilot Study," *Ann. Rheum. Dis.*, 62(1); 239-240 (2003) and EULAR—Annual European Congress of Rheumatology, Lisbon, Portugal (2003) (abstract).

Nikas, S.N., et al., "Treatment of Resistant Rheumatoid Arthritis by Intra-Articular Injections with Infliximab: A Pilot Study," *Ann. Rheum. Dis.* 62(1): 408 (2003) and EULAR—Annual European Congress of Rheumatology, Lisbon, Portugal (2003) (abstract).

Salin, M.L. and McCord, J.M., "Free Radicals and Inflammation: Protection of Phagocytosing Leukocytes by Superoxide Dismutase," *J. Clin. Invest.*, 56:1319-1323 (1975).

Schalkwijk, J. et al., "Cationization of Catalase, Peroxidase, and Superoxide Dismutase," *J. Clin. Invest.*, 76:198-205 (1985).

Steer, J.H. et al., "Altered Leucocyte Trafficking and Suppressed Tumour Necrosis Factor α Release from Peripheral Blood Monocytes After Intra-Articular Glucocorticoid Treatment," *Ann. Rheum. Dis.*, 57(12): 732-737 (1998).

Stepanik, T.M. and Ewing, D.D., "Coisolation of Glutathione Peroxidase, Catalase and Superoxide Dismutase from Human Erythrocytes," *J. Biochem. Biophys. Methods*, 20:157-169 (1990).

Tiku, M.L. et al., "Aggrecan Degradation in Chondrocytes is Mediated by Reactive Oxygen Species and Protected by Antioxidants," *Free Radic. Res.*, 30:395-405 (1999).

Tiku, M.L. et al., "Evidence Linking Chondrocyte Lipid Peroxidation to Cartilage Matrix Protein Degradation," *J. Biol. Chem.*, 275(26):20069-20076 (2000).

Trif, M. et al., "Liposomes as Possible Carriers for Lactoferrin in the Local Treatment of Inflammatory Diseases," *Exp. Biol. Med.*, 226(6):559-564 (2001).

Williams, A.S. et al., "Amelioration of Rat Antigen-Induced Arthritis by Liposomally Conjugated Methotrexate is Accompanied by Down-Regulation of Cytokine mRNA Expression," *Rheumatology*, 40:375-383 (2001).

Yang, J.G. et al., "Purification and Quantitation of a Rat Plasma Selenoprotein Distinct from Glutathione Peroxidase Using Monoclonal Antibodies," *J. Biol. Chem.*, 262(27):13372-13375 (1987).

El-Khoury, G., et al., "Percutaneous Procedures for the Diagnosis and Treatment of Lower Back Pain: Diskography, Facet-joint Injection, and Epidural Injection," *AJR*, 157(4): 685-691 (1991).

Gori, A., et al., "Tumor Necrosis Factor-α Increased Production During Thalidomide Treatment in Patients With Tuberculosis and Human Immunodeficiency Virus Coinfection," *The Journal of Infectious Diseases*, 182: 639 (2000).

McMillan, D., et al., "Intra-operative Autologous Blood Management," *Transfusion and Apheresis Science*, 27(1): 73-81 (2002).

Okuma, M., et al., "Rotary Cell Culture System Stimulates Annulus Fibrosus Cell Proliferation but Suppresses Proteoglycan Metabolism," 164, *Abstracts of the 30th Annual Meeting of the International Society for the Study of the Lumbar Spine*, Vancouver, Canada (May 2003).

Risbud, M., et al., "Mesenchymal Stem Cells Respond to Their Microenvironment in Vitro to Assume Nucleus Pulposus-like Phenotype," 26, *Abstracts of the 30th Annual Meeting of the International Society for the Study of the Lumbar Spine*, Vancouver, Canada (May 2003).

Castro, R., et al., "Failure of Bone Marrow Cells to Transdifferentiate Into Neural Cells in Vivo," *Science*, 297: 1299 (2002).

U.S. Appl. No. 12/005,069, filed Dec. 21, 2007.
U.S. Appl. No. 12/291,378, filed Nov. 7, 2008.
U.S. Appl. No. 12/290,998, filed Nov. 5, 2008.
U.S. Appl. No. 12/291,016, filed Oct. 31, 2008.

Ando, N., et al., "An Immunohistochemical Study of the Degenerative Lumbar Disc," *Orthopedics & Traumatology* 44(1): 176-178 (1995) (Published in Japanese with English Abstract).

Blight, A.R., "Miracles and molecules—progress in spinal cord repair," *Nature Neuroscience Supplement* 5:1051-1054 (Nov. 2002).

Höke, A., "Mechanisms of Disease: what factors limit the success of peripheral nerve regeneration in humans?," *Nature Clinical Practice Neurology* 2(8): 448-454 (Aug. 2006).

Marzo-Ortega, H., et al., "Bone mineral density improvement in spondyloarthropathy after treatment with etanerecept," *Ann. Rheum. Dis.* 62: 1020-1021 (2003).

Muthumani, K., et al., "Suppression of HIV-1 viral replication and cellular pathogenesis by a novel p38/JNK kinase inhibitor," *AIDS* 18:730-748 (2004).

Schmidt, C.E. and Leach, J.B., "Neural Tissue Engineering: Strategies for Repair and Regeneration," *Annu. Rev. Biomed. Eng.* 5:293-347 (Jun. 2003).

't Hart, B.A. and Amor, S., "The use of animal models to investigate the pathogenesis of neuroinflammatory disorders of the central nervous system," *Curr. Opin. Neurol.* 16:375-383 (2003).

Yorimitsu, E., "A Comparative Study on the Pathological Changes of Intervertebral Discs after Intradiscal Injection of Various Kinds of Steroid Materials: An Experimental Study," *Journal Keio Medical Society* 74(5): 303-315 (1997) (Published in Japanese with English Abstract).

International Preliminary Report on Patentability, PCT/US2004/039589, mailed Jun. 8, 2006.

International Search Report and Written Opinion, PCT/US2004/039589, mailed Jul. 14, 2005.

Invitation to Pay Additional Fees with Partial International Search, PCT/US2004/039589, mailed Apr. 22, 2005.

Communication pursuant to Article 96(2) EPC, EP 04 812 165.1, mailed Aug. 21, 2007.

Communication pursuant to Article 94(3) EPC, EP 04 812 165.1, mailed Aug. 19, 2009.

Dernis, E., et al., "Infliximab in spondylarthropathy-Influence on bone density," *Clinical and Experimental Rheumatology*, 20 (Suppl. 28): S-185-S-186 (2002).

Brekke, O.H. and Sandlie, I, Therapeutic Antibodies for Human Diseases at the Dawn of the Twenty-First Century, Nature Reviews, 2, 52-62 (2003).

(56) References Cited

OTHER PUBLICATIONS

Hotten et al., "Recombinant Human Growth Differentiation Factor 5 Stimulates Mesenchyme Aggregation and Chondrogenesis Responsible for the Skeletal Development of Limbs Growth Factors," 13: 65-74 (1996).

Van Beuningen, H.M., et al., "Differential Effects of Local Application of BMP-2 or TGF-B1 on Both Articular Cartilage Composition and Osteophyte Formation," Osteoarthritis and Cartilage, 6: 306-317 (1998).

Weinblatt, M.E., et al. Adalimumab, A Fully Human Anti-Tumor Necrosis Factor Alpha Monoclonal Antibody, for the Treatment of Rheumatoid Arthritis in Patients Taking Concomitant Methotrexate, Arthritis and Rheumatism, 48(1), 35-45 (2003).

He Yong, "The connection of IL-6 and TNF-α with postmenopausal osteoporosis," *Section Endocrinal Foreign Med Sci*, 23(2): 130-132 (Mar. 2003).

* cited by examiner

H

H   FGF

H   FGF   ARA

← TIME →

INSERT CARRIER

INSERT CANNULA

INSERT BFA, THROUGH CARRIER

LOCAL INTRAOSSEOUS ADMINISTRATION OF BONE FORMING AGENTS AND ANTI-RESORPTIVE AGENTS, AND DEVICES THEREFOR

BACKGROUND OF THE INVENTION

Osteoporosis is a disease that results in the weakening of bone and an increase in the risk of fracture. It has been reported that American females over the age of 50 have about a 50% chance of breaking a bone during their lifetime, and a 40% chance of breaking either a hip, vertebra or wrist. Postmenopausal women lose about 1-3% of their bone mass for each of the first 5-7 years after menopause. Osteoporosis is believed to contribute to about 1.5 million fractures a year in the United States, including about 700,000 spinal fractures and about 300,000 hip fractures. According to the Mayo Clinic, about 25% of the people over 50 who fracture a hip die within a year of the incident. The risk of breaking a bone for an osteoporotic individual doubles after the first fracture. The risk of breaking a second vertebra for an osteoporotic individual increases about four-fold after the first spinal fracture.

Human bone comprises hard mineralized tissue and softer collagenous tissue. The combination of these tissues provides bone with both a structural, weight-bearing capability and a shock-absorption capability. As the bone ages, however, the collagenous portion of the bone is slowly mineralized, thereby making the entire bone more brittle. To compensate for this, bone constantly undergoes a process called "remodeling" in which older, more mineralized bone is replaced by new, more collagenous bone.

Bone remodeling is undertaken by two competing processes: bone formation and bone resorption. Bone formation is largely achieved by bone-forming cells called osteoblasts, while bone resorption is largely achieved by bone-eating (bone-resorbing) cells called osteoclasts. In the normal desired situation, the rate of bone formation is essentially equal to the rate of bone resorption, so that bone mass in the body is maintained.

Osteoporosis occurs when the rate of bone resorption exceeds the rate of bone formation. The rate of bone resorption is largely dependent upon the local production of osteoclasts.

Current treatments for osteoporosis have focused upon arresting the activity of the osteoclast cells. In particular, osteoporosis therapy has focused upon administering drugs called "anti-resorptive agents" or ARA's. The most common classes of anti-resorptive drugs include estrogen, selective estrogen receptor modulators (SERMs), biphosphonates, calcitonin, osteoprotegrin (OPG), cathespin K and statins. Current products include FOSAMAX® (alendronate) in the U.S., Biphosphonate DIDRONEL® (etidronate), and ACTONEL® (risedronate).

Despite the promise provided by these anti-resorptives, there still remain serious issues. First, many anti-resorptives act in a manner that wholly eliminates osteoclast activity. Thus, the delicate balance between bone formation and bone-resorption is again upset, and older, highly mineralized tissue remains within the bone. Although this has the effect of increasing bone mineral density (BMD), the bone that remains is fragile and prone to microdamage.

Second, many of the anti-resorptives are administered systemically, through either oral or intravenous means. Accordingly, side effects associated with systemic administration are often seen. For example, the systemic administration of hormone replacement therapy ("HRT") has been associated with an elevated cancer risk. In response to this concern, some anti-resorptive drugs, such as biphosphonates, have been engineered to be selective for bone tissue. However, in many cases, the amount of such tissue selective drug that actually reaches the bone is often less than 100%.

In recent years, the roles of estrogen and pro-inflammatory cytokines in osteoporosis have become much more clear. For example, in post-menopausal women, it is believed that osteoporosis occurs due to a decrease in estrogen. Because estrogen is believed to block the production of pro-inflammatory cytokines, a depleted level of estrogen is believed to lead to an increase in pro-inflammatory cytokines, and consequently to increased osteoclast production and increased bone resorption.

Pacifici, R., "Cytokines, estrogen, and postmenopausal osteoporosis—the second decade," *Endocrinology*, 139(6): 2659-2661 (1998), teaches that estrogen prevents bone loss by blocking the production of proinflammatory cytokines by bone marrow and bone cells. Pacifici further discloses that IL-1 and TNF-α are the most powerfully locally produced stimulators of bone resorption and are well recognized inhibitors of bone formation. Pacifici concludes that there is now substantial evidence supporting the hypothesis that a network of estrogen-regulated cytokines is responsible for the changes in bone turnover and the loss of bone induced by estrogen deficiency, and that it is likely that during the current decade the development of orally active, tissue selective cytokine inhibitors will lead to new strategies for the prevention and treatment of postmenopausal osteoporosis. As Pacifici discloses only oral administration, Pacifici does not disclose the local administration of selective cytokine inhibitors.

Allali, F., et al., "Increase in bone mineral density of patients with spondyloarthropathy treated with anti-tumour necrosis factor alpha," *Ann. Rheum. Dis.*, 62: 347-349 (2003) reports of an increase in the bone mineral density (BMD) of patients with spondyloarthropathy (SpA) treated with anti-tumor necrosis factor α (TNF-α). Patients in the Allali study received infliximab by infusion. Allali suggests that a benefit of the anti-TNF-α therapy on BMD in patients with SpA may be through an uncoupling effect on bone cells. Allali does not disclose the local administration of selective cytokine inhibitors.

Published U.S. Patent Application No. U.S. 2003/0007972 ("Tobinick I") discloses methods for treating bone metastases in humans by locally administering a therapeutically effective dose of specific cytokine inhibitors. Tobinick discloses local administration routes designed for perilesional or intralesional use in proximity to the site of tumor metastases to bone, including subcutaneous, intramuscular, interspinous, epidural, peridural, parenteral or perispinal administration.

Tobinick, E. L., "Targeted etanercept for treatment-refractory pain due to bone metastasis: two case reports," *Clin. Ther.*, 25(8): 2279-88 (2003) ("Tobinick II") discloses that etanercept delivered by targeted SC injection may be of clinical benefit in selected patients with treatment-refractory pain caused by bone metastases.

Tobinick does not disclose the intraosseous administration of selective cytokine inhibitors, nor does Tobinick disclose treating osteoporotic bone.

In sum, no prior art reference discloses an intraosseous injection of a highly specific cytokine antagonist (i.e., inhibitor) inhibitor to increase i.e., the BMD of an uncoupled resorbing bone.

Because of the limitations of anti-resorptives, some investigators have focused on increasing bone-formation activity as a means of treating osteoporosis. For example, teriparatide (hPTH 1-34), a fragment of parathyroid hormone, has been found to increase the rate of bone formation and has been approved for treating osteoporosis. However, it must be taken as a daily intravenous injection. In addition, according to Biskobing, D. M., "Novel therapies for osteoporosis," *Expert Opinion Invest. Drugs*, 12(4): 611-621 (2003), the FDA has recommended a maximum of 2 years of treatment due to concern over long-term safety in light of the development of osteosarcoma in rats treated with high-dose teriparatide. See also Vahle, J. L., et al., "Skeletal changes in rats given daily subcutaneous injections of recombinant human parathyroid hormone (1-34) for 2 years and relevance to human safety," *Toxicol Pathol.*, 30(3): 312-21 (2002).

Other investigators have proposed administering selected growth factors as a means of increasing the rate of bone formation. For example, Rodan, G. A. and Martin, T. J., "Therapeutic approaches to bone diseases," *Science*, 289: 1508-1514 (2000) ("Rodan") proposes that growth factors such as insulin-like growth factor (IGF), transforming growth factor-β (TGF-β) fibroblast growth factor (FGF), and bone morphogenic proteins (BMPs) have come under consideration as potential treatments for bone diseases, especially severe osteoporosis. Rodan further noted that future developments might yield ways to overcome conventional difficulties by confining these growth factors to bone sites through osteoblast-targeted regulation of their production, or, perhaps, by gene therapy. However, some of these growth factors may also have an effect of upregulating osteoclast activity as well.

Because of its potential as a bone growth agent, a number of investigators have investigated the use of fibroblast growth factor (FGF) as a bone forming agent.

Nakamura, K., et al., "Local application of basic fibroblast growth factor into the bone increases bone mass at the applied site in rabbits," *Arch. Orthop. Trauma Surg.*, 115(6): 344-346 (1996), ("Nakamura") discloses that a single local injection of basic fibroblast growth factor (bFGF) into a rabbit ilium causes local bone growth.

Lane, N. E., et al., "Basic fibroblast growth factor forms new trabeculae that physically connect with pre-existing trabeculae, and this new bone is maintained with an anti-resorptive agent and enhanced with an anabolic agent in an osteopenic rat model," *Osteoporosis Int'l.*, 14: 376-82 (2003) ("Lane") discloses that a systemic administration of bFGF induces bone growth in the proximal tibia of ovarectomized ("OVX") rats. Lane further reports that the bone growth caused by the bFGF appears to resorb in these OVX rats after the administration period. Lastly, Lane reports that a post-FGF systemic administration of hPTH (1-34) was effective in maintaining the bone growth attributable to the FGF administration.

Goodman, S. et al., "Effects of local infusion of TGFbeta on bone ingrowth in rabbit chambers," *J. Biomed. Mat. Res.* (*Appl Biomater*), 53: 475-479 (2000) teaches the local delivery of TGF-B in rabbit chambers.

Some investigators have advocated a combination therapy including a bone-forming agent and an anti-resorptive. For example, Biskobing further noted that others have recommended using teriparatide concomitantly with an anti-resorptive. Rodan, "Therapeutic approaches to bone diseases," *Science*, 289: 1508-1514 (2000) concluded that far less attention has been paid to promoting bone formation with, for example, growth factors or hormones, an approach that would be a valuable adjunct therapy to patients receiving inhibitors of bone resorption.

U.S. Pat. No. 6,554,830 ("Chappius") discloses a surgical anchor for anchoring within a vertebral body, having a plurality of passages for the delivery of bone cement therethrough. Specified bone bonding cements appear to include polymethylmethacrylate and cranial plast.

U.S. Published Patent application No. U.S. 2002/0010471 ("Wironen") discloses methods of injecting materials into osteoporotic bones. In particular, Wironen is directed to a device for injecting materials into bone comprising a threaded catheter and an internal removable trocar. The subject device may also have disposed on one end an attachment means, e.g., Luer-lock fitting, for attaching a syringe, whereby a syringe of any filler can then be attached to the luer-lock fitting and the filler material can then be squirted through the catheter and into the marrow cavity. One filler that may be used is a composition comprising mineralized particles (e.g., corticocancellous chips or "CCC" of a size from about 100 to 1000 microns, e.g., 500 to 850 microns), ground bone powder (for example, from about of 100 to 1000 microns, e.g., 500 to 850 microns), a biactive ceramic such as a non-degradable or degradable hydroxyapatite, bioactive glass, and the like, osteogenic paste, chondrogenic paste, carrier associated Growth Factors, carrier associated mineralized particles, morsellized skin or other tissue, Fibrin powder, Fibrin/plasminogen glue, Demineralized Bone Matrix (DBM)/glycerol, DBM/pleuronic F127, DBM/CCC/F127, polyesters, polyhydroxy, compounds, polyvinyl compounds, polyamino compounds, polycarbonate compounds, and mixtures of one or more of these compositions. Wironen further teaches that the resulting repair using this bone paste composition leads to a mass of mineralized tissue that is vascularized. When non-degradable hydroxapatite is used, the mass is stable and not as subject to degradation by the osteoporotic patient. Wironen does not disclose anti-resorptive materials.

Accordingly there is a need to provide improved methods of treatment of osteoporosis and related diseases.

SUMMARY OF THE INVENTION

The present invention provides compositions, formulations, methods and devices for treating osteoporosis. The present inventors have appreciated a) the desirability of providing local administration of osteotherapeutic drugs, b) the desirability of sustaining the bone-forming activity in an osteopenic or osteoporotic bone, and c) the desirability of restoring to pre-osteoporosis levels the bone-resorbing activity in a bone suffering from the disease of osteoporosis.

Providing local administration of an osteotherapeutic drug is desirable because the local nature of the injection of the drug will significantly mitigate the risk that the drug will cause unwanted side effects outside of the target bone. Restricting delivery to the local area also allows the drug to be delivered in a higher concentration than would normally be used in a systemic administration, thereby increasing the residence time and the potency of the therapeutic amount of the drug. In addition, without wishing to be tied to a theory, since the cortical shell of the bone comprises a relatively dense structure, this outer component of the bone may prevent the out-diffusion of the drug and so may provide a suitable depot for the osteotherapeutic drug, thereby increasing its half-life in the target bone.

Administering a bone-forming agent is desirable because there is a heightened risk of fracture in osteopenic or osteoporotic bone and administration of the bone forming agent into that bone will cause new bone growth within the osteopenic or osteoporotic bone. This bone growth will increase the strength of the bone and thereby reduce the risk of its fracture.

Administering an anti-resorptive agent (ARA) is desirable because it will help restore the proper and desirable balance between bone formation and bone resorption in the bone suffering from osteoporosis even after the bone-forming agent (BFA) has been depleted. Accordingly, the bone growth provided by the BFA will be maintained indefinitely.

Accordingly, in one aspect of the present invention, the present inventors have developed a method of therapeutically treating an uncoupled resorbing bone in a patient, comprising the steps of:
   a) locally administering an effective amount of a first formulation comprising a bone-forming agent into the bone, and
   b) locally administering an effective amount of a second formulation comprising an anti-resorptive agent into the bone.

The present inventors have also appreciated the many benefits of providing local intraosseous administration of a highly specific cytokine antagonist as an anti-resorptive agent.

First, since it is known that many cytokines (such as selected interleukins and TNF-α) play roles in mediating the upregulation of osteoclast production, injecting an antagonist or inhibitor of these proteins directly into the uncoupled resorbing bone prevents the target cytokine from inducing any further osteoclast upregulation. In effect, the intraosseous administration of the cytokine antagonist arrests the bone resorption process of the uncoupled resorbing bone, returning it to a more coupled and balanced state. Preferably, this aspect of the present invention seeks to treat the uncoupled resorbing bone before it fractures.

Second, since the high specificity cytokine antagonist (HSCA) inhibits only the specific cytokine(s) of interest, the HSCA may be combined with other therapeutic agents (such as bone growth agents, e.g., FGF or mesenchymal stem cells) that can also be injected into the bone without reducing the effectiveness of those other agents.

Third, without wishing to be tied to a theory, since the cortical shell of the bone comprises a relatively dense structure, intraosseous administration of the HSCA through this outer component of the bone may provide a suitable depot for the high specificity cytokine antagonist (HSCA), thereby possibly increasing its half-life in the disc.

Fourth, since it is believed that many of the problematic cytokines are actually secreted by either bone marrow or bone cells, intraosseous injection of the high specificity antagonists will advantageously attack the problematic cytokines at their source of origination.

Accordingly, in another aspect of the present invention, there is provided a method of treating osteoporosis in a patient, comprising locally administering an effective amount of a formulation comprising an effective amount of a highly specific cytokine antagonist into an uncoupled resorbing bone.

Accordingly, in another aspect of the present invention, there is provided a kit for treating osteoporosis, comprising:
   a) an effective amount of a bone forming agent, and
   b) an effective amount of a highly specific cytokine antagonist.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
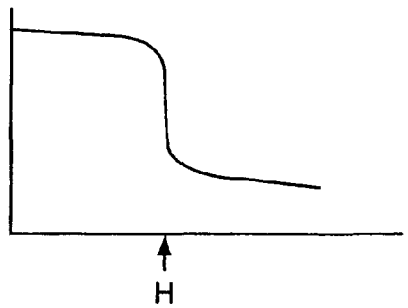
FIG. 1 is a graph of the effect on bone tissue mass when bone resorption exceeds bone formation, as in the case of estrogen withdrawal. H: hysterectomy.

A description of preferred embodiments of the invention follows.

For the purposes of the present invention, the terms "inhibitor" and antagonist" are used interchangeably. A protein may be inhibited at the synthesis level, at the translation level, by shedding, by antibodies, or by soluble receptors. The term "patient" refers to a human having an uncoupled resorbing bone. A patient having "osteopenic" bone has a bone mineral density that is less than the mean bone mineral density (BMD) for that patient's age and sex. A patient having "osteoporotic" bone has a bone mineral density that is less than two standard deviations below the mean for that patient's age and sex. "Local" and "intraosseous" administration are used interchangeably. A "BF agent" or "BFA" is a bone-forming agent. An "AR agent" or "ARA" is an anti-resorptive agent. "OP" refers to the disease of osteoporosis.

For the purposes of the present invention "intraosseous administration" is a local administration and includes, but is not limited to:
a) injecting a formulation into the cancellous portion of an uncoupled resorbing bone, such as a relatively intact vertebral body,
b) injecting a formulation into the cortical portion of an uncoupled resorbing bone,
c) providing a formulation in a patch attached to an outer wall of the bone,
d) providing a formulation in a depot at a location outside but closely closely adjacent to an outer wall of the bone,
e) providing the formulation in a depot at a location outside but closely adjacent to an endplate of a vertebral body ("trans-endplate administration"),
f) injecting the formulation into a local artery that substantially empties into the target bone,
g) mixing the formulation with cement and injecting it into the target area, and
h) delivering the formulation via metallic or non-metallic bone fracture fixation devices/pumps to the target tissue.

Other modes of administration include parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal and transdermal. In some embodiments, the ARA is administered systematically.

Because osteoporosis is a continuous process, the bone to which the therapeutic drug is administered may be in any one of a number of states. In general, the bone should be characterized as uncoupled resorbing bone. For the purposes of the present invention, the bone remodeling processes in "uncoupled resorbing bone" are such that bone resorption exceeds bone formation, thereby leading to osteopenic and eventually, in some cases, osteoporotic bone. Accordingly, the bone may be an intact bone or it may be fractured (such as a vertebral body compression fracture). It may be osteoporotic (defined as having a bone mineral density (BMD) of at least 2 standard deviations below normal bone mineral density for that patient's age and sex), it may be osteopenic or it may have normal bone mineral density (BMD). In some instances, the uncoupling has existed for a time sufficient to produce osteoporotic bone. In other instances, the uncoupling has existed for only a relatively short time and so the bone is osteopenic or normal.

In some embodiments, the target bone consists essentially of healthy tissue. In other embodiments, the target bone is tumorous.

In some embodiments, the target bone is intact. In other embodiments, the target bone is fractured.

The patient may have type I osteoporosis, wherein bone resorption rates exceed normal values, so that bone resorption exceeds bone formation. In some embodiments thereof, the patient may be peri-menopausal. In some embodiments thereof, the patient may be post-menopausal. In each menopausal case, the patient is characterized as having an estrogen deficiency.

The patient may have type II osteoporosis, wherein bone formation rates fall below normal values.

In some embodiments, the bone into which the formulation is administered is a vertebral body. In some embodiments, the vertebral body is a cervical vertebral body.

In some embodiments, the vertebral body is a thoracic vertebral body. In some embodiments, the vertebral body is a lumbar vertebral body.

Since the vertebral body often fails by a crushing of its anterior portion, it would be advantageous to ensure that bone growth occurs in the anterior portion of the vertebral body. In some embodiments, the formulation is administered into the anterior half of the vertebral body. In some embodiments, the formulation is administered into the most-anterior third of the vertebral body. In some embodiments, the formulation is administered into the most-anterior quarter of the vertebral body. In some embodiments, the formulation is administered into a non-fractured vertebral body and is adjacent to a fractured vertebral body.

In conventional vertebroplasty, it has been found that the treatment of a fractured vertebral body with high stiffness materials such as polymethylmethacrylate (PMMA) often causes increased stress upon the intact adjacent vertebral bodies, often leading to the eventual fracture of those adjacent levels. Accordingly, in some embodiments, the formulation is administered into an intact vertebral body that is adjacent to an augmented vertebral body.

Examination of the sites of vertebral body compression fracture reveals a high prevalence of fracture at the two specific vertebrae at the thoraco-lumbar junction. In particular, the literature has reported that fracture of either the T12 or the L1 vertebra accounts for between about one-third to one-half of all vertebral body compression fractures. Accordingly, in some embodiments, local intraosseous administration is provided to a vertebra selected from the group consisting of the T12 and the L1 vertebrae. In some embodiments, each of the T12 and the L1 vertebrae are provided with local intraosseous administration.

In some embodiments, only the T12 and L1 vertebrae are provided with local intraosseous administration. These embodiments have the advantage of providing therapy to the two vertebra at most risk of fracture. Consequently, up to half of the vertebral body compression fractures could be eliminated by treating only two of the 22 vertebrae present in the human spine.

In some embodiments, each vertebra from T6 to L3 is provided with intraosseous local administration. The literature has reported that about 90% of all vertebral body compression fractures occur within this region of the spine. Consequently, about 90% of all vertebral body compression fractures could be eliminated by treating only about half of the 22 vertebrae present in the human spine.

In some embodiments, each of the vertebrae from T4 to L5 is provided with intraosseous local administration. The literature has reported that essentially all of the vertebral body compression fractures occur within this region of the spine.

In some embodiments, the bone into which the formulation is administered is a femur. In some embodiments thereof, the formulation is administered into the head of the femur. In some embodiments thereof, the formulation is administered into the neck of the femur.

In some embodiments, the formulation is administered into an intact hip (i.e., hip bone). In some embodiments, the formulation is administered into a fractured hip. In some embodiments, the formulation is administered into an intact hip adjacent to a fractured hip.

In some embodiments, the target tissue is a human bone selected from the group consisting of a foot, an ankle, a wrist (e.g., preferably, a distal radius) and a tibia (e.g., either a proximal portion or a distal portion).

In some embodiments, the formulation of the present invention is administered directly into the bone through the outer cortical wall of the bone. In one embodiment, the direct administration includes depositing the BF and/or AR agent into the cancellous portion of the bone. In this condition, the dense nature of the cortical wall that surrounds the cancellous portion will help keep the BF and/or AR agent contained within the bone. In one embodiment, the direct administration includes depositing the BF and/or AR agent into the cortical portion of the bone.

FIG. 1 is a graph of the inventors' understanding of the change in bone tissue mass when bone resorption exceeds bone formation. This condition may occur after, for example, estrogen withdrawal. Estrogen withdrawal may occur in women after a hysterectomy or after menopause.

As shown in the Figure, shortly after estrogen withdrawal, there is a noticeable decrease in bone tissue mass. Without wishing to be tied to a theory, it is believed that estrogen withdrawal causes an upregulation of cytokines such as TNF-α, which, in turn, causes an upregulation of osteoclast production. The increased osteoclast production causes an uncoupling of the bone remodeling process, resulting in net bone loss. Impaired bone function is also involved. This decrease in bone function might be due to a decrease in local IGF-1 and/or TGF-β production.

Figure 2:
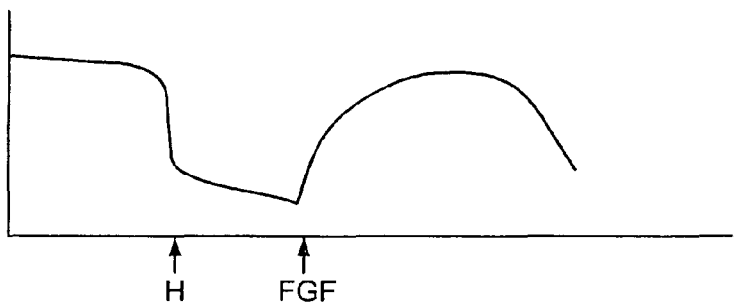
FIG. 2 is a graph showing the transient effect of a one-time addition of a bone forming agent to the bone of FIG. 1. H: hysterectomy. FGF: fibroblast growth factor.

FIG. 2 is a graph of the inventors' understanding of the change in bone tissue mass when a bone growth agent such as basic fibroblast growth factor (bFGF) is administered after estrogen withdrawal. As shown in the Figure, the bone growth agent effectively causes bone growth to occur for a certain period of weeks. Without wishing to be tied to a theory, it is believed that administration of the BF agent causes increased bone growth, thereby offsetting the increased bone resorption caused by estrogen withdrawal, resulting in net bone gain. After this short period of weeks, however, the gradual depletion of the BF agent from the tissue (either through consumption or vascular elimination) returns the bone remodeling process to its essentially normal balanced state. After still more time, the continued depletion of the BF agent returns the bone remodeling process to a resorbing one resulting in continued bone loss. Simply, locally providing a bone growth agent to an osteoporotic bone may result in only a temporary bone gain.

Figure 3:
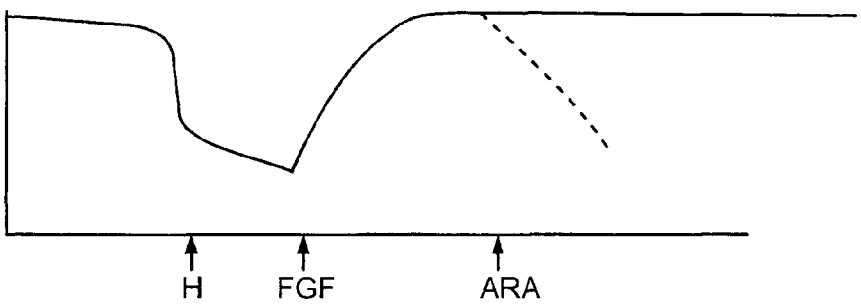
FIG. 3 is a graph showing the lasting effect of the continuous presence of an anti-resorptive agent added to the bone of FIG. 2. H: hysterectomy. FGF: fibroblast growth factor. ARA: anti-resorptive agent.

FIG. 3 is a graph of the inventors' understanding of the change in bone tissue mass when an anti-resorptive agent (such as an anti-TNF agent) is continuously administered after administration of the bone forming agent has ceased. As shown in the Figure, the AR agent effectively maintains the bone growth initially provided by the bone growth agent. Without wishing to be tied to a theory, it is believed that continuous administration of the AR agent at least partially inhibits the osteoclasts, thereby maintaining the bone remodeling process in a neutral state and, preferably, resulting in a net steady state bone condition for at least as long as the AR agent is administered.

In some embodiments, at least the AR agent is provided in at least intermittent (and more preferably, continuous) administration. According to some investigators, such as Lane, the mere delivery of a BF agent will serve to only increase bone tissue in the short term (e.g., a few weeks). The reason for this is that, after the BF agent has been depleted, the target bone returns to its uncoupled state and so osteoclast activity again predominates. Therefore, it is advantageous to provide the AR agent in a plurality of administrations. In some embodiments, the administrations span at least one month. In other embodiments, they span at least two months, for example, at least three months, or at least six months, or at least 12 months.

In one embodiment, at least the AR agent is provided in continuous administration. Since bony tissue is highly vascular (and osteoporotic tissue even more so), providing only intermittent administration runs the risk that the AR agent will be depleted before the next administration. Therefore, it is advantageous to provide the AR agent in a continuous administration. In some embodiments, the continuous administration spans at least one month, for example, at least two months, or at least three months, or at least six months, or at least 12 months.

BF agent and AR agent are administered simultaneously. In others, the BF agent is administered first. In still others, the AR agent continues to be administered after the administration of the BF agent has ceased. In some embodiments, the AR agent is administered first.

In some embodiments, the BF agent comprises a growth factor.

In some embodiments, two BF agents are administered, for example, sequentially.

In some embodiments, the first BF is a growth factor and the second BF agent is an anabolic agent. According to Lane, supra, initial administration of FGF results in the growth of spinculues and an increase in trabeculae connectivity, while later administration of hPTH (1-34) increases bone mass.

In some embodiments, two growth factors are administered, for example, sequentially. In some embodiments thereof, the first BF agent is an angiogenic growth factor and the second BF agent is an osteoinductive growth factor. According to U.S. Pat. No. 5,270,300 ("Hunziker"), the specification of which is incorporated herein by reference in its entirety, the sequential administration of these agents has the benefit of first providing for neovascularization that is critical to bone growth. According to Hunziker, the sequential administration of these factors resulted in superior bone growth. Preferred angiogenic growth factors include FGF, PDGF and TGF.

In some embodiments, three BF agents are administered, for example, sequentially.

Figure 4:
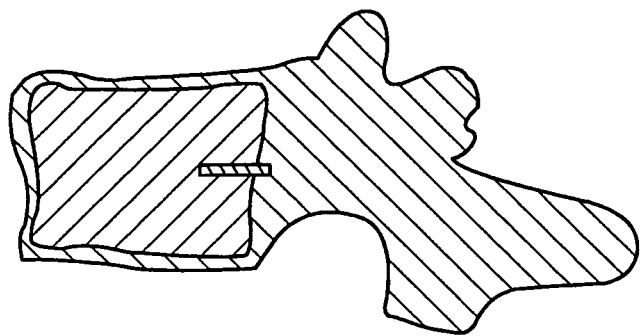
FIG. 4 is a cross-section of a human hip having a device of the present invention implanted therein.
Figure 5:
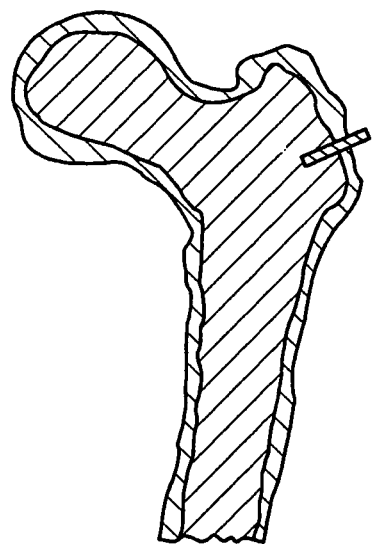
FIG. 5 is a cross-section of a human hip having a device of the present invention implanted therein.

FIG. 4 is a cross-section of a human hip having a device of the present invention implanted therein. FIG. 5 is a cross-section of a human hip having a device of the present invention implanted therein.

FIGS. 6A-F provide a number of administration scenarios considered to be useful in treating osteoporosis.

Figure 6A:
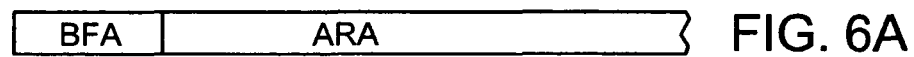
FIGS. 6A-F disclose some preferred administration sequences of the present invention. BFA: bone forming agent. ARA: anti-resorptive agent. GF: growth factor.

FIG. 6A discloses a therapy comprising an initial, short-term administration of a bone forming agent followed by a long term administration of an AR agent. The rationale for this therapy is to initially provide the patient with a bone forming agent to grow bone. However, since bone growth often takes only about one month to occur, the BF agent need not be administered after the first month. The subsequent administration of the AR agent insures that the bone grown during the first month remains.

Figure 6B:
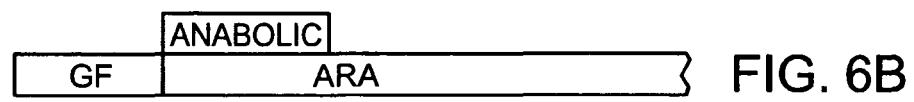

FIG. 6B discloses a therapy comprising an initial, short-term administration of a growth factor followed by concomitant administration of an AR agent and an anabolic agent. The rationale for this therapy is to initially provide the patient with newly built trabeculae-forming bridges that physically connect existing trabeculae. The subsequent administration of the AR agent and the anabolic agent (such as hPTH 1-34) respectively allows the newly grown bone to be maintained and allows additional growth to be added.

Figure 6C:
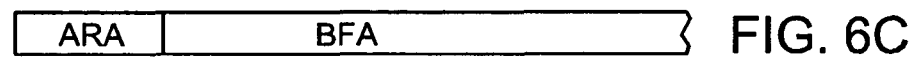

FIG. 6C discloses a therapy comprising an initial, short-term administration of an AR agent followed by administration of a BF agent. The rationale for this therapy is to initially restore the bone remodeling balance that had been disrupted by the osteoporosis. The administration of a HSCA is particularly preferred in this respect. After the balance has been restored, the bone growth agent is administered, thereby uncoupling the bone to produce bone growth.

Figure 6D:

FIG. 6D follows the initial steps of FIG. 6C, but adds a subsequent administration of an AR agent. This therapy recognizes that, without a long term administration of an AR agent, the bone formed due to administration of the BF agent may be resorbed due to the underlying osteoporosis.

Figure 6E:
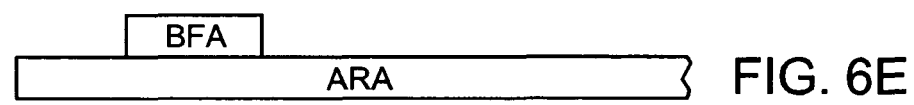

FIG. 6E follows the rationale of FIG. 6D, but simply provides for a continuous administration of the AR agent. This therapeutic regimen may allow for a simpler delivery device.

Figure 6F:

FIG. 6F follows the rationale of FIG. 6E, but further provides for a continuous administration of the AR agent. This therapeutic regimen may allow for an even simpler delivery device, such as the device of FIG. 7.

In general, the first formulation optionally comprises an effective amount of a bone forming agent. The bone-forming agent may be:
- a) a growth factor (such as an osteoinductive or angiogenic factor),
- b) osteoconductive (such as a porous matrix of granules),
- c) osteogenic (such as viable osteoprogenitor cells), or
- d) plasmid DNA.

In some embodiments, the formulation comprises a liquid carrier, and the bone forming agent is soluble in the carrier.

In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including MP-52; HBGF-1 and HBGF-2; growth differentiation factors (GDFs), members of the hedgehog family of proteins, including indian, sonic and desert hedgehog; ADMP-1; bone-forming members of the interleukin (IL) family; GDF-5; and members of the colony-stimulating factor (CSF) family, including CSF-1, G-CSF, and GM-CSF; and isoforms thereof.

In some embodiments, the growth factor is selected from the group consisting of TGF-β, bFGF, and IGF-1. These growth factors are believed to promote the regeneration of bone. In some embodiments, the growth factor is TGF-β. More preferably, TGF-β is administered in an amount of between about 10 ng/ml and about 5000 ng/ml, for example, between about 50 ng/ml and about 500 ng/ml, e.g., between about 100 ng/ml and about 300 ng/ml.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are intraosseously administered into the target bone. In some embodiments, between about 1 microgram (μg) and about 1 mg of BMP are intraosseously administered into the target bone.

In some embodiments, the bone forming agent comprises an effective amount of a fibroblast growth factor (FGF). FGF is a potent mitogen and is angiogenic, and so attracts mesenchymal stem cells to the target area. It is further believed that FGF stimulates osteoblasts to differentiate into osteocytes.

In some embodiments, the FGF is acidic FGF (aFGF).
In some embodiments, the FGF is basic FGF (bFGF).

In some embodiments, between about 1 microgram (μg) and about 10,000 μg of FGF are intraosseously administered into the target bone. In some embodiments, between about 10 μg and about 1,000 μg of FGF are intraosseously administered into the target bone. In some embodiments, between about 50 μg and about 600 μg of FGF are intraosseously administered into the target bone.

In some embodiments, between about 0.1 and about 4 mg/kg/day of FGF are intraosseously administered into the target bone. In some embodiments, between about 1 and about 2 mg/kg/day of FGF are intraosseously administered into the target bone.

In some embodiments, FGF is intraosseously administered into the target bone in a concentration of between about 0.1 mg/ml and about 100 mg/ml. In some embodiments, FGF is intraosseously administered into the target bone in a concentration of between about 0.5 mg/ml and about 30 mg/ml. In some embodiments, FGF is intraosseously administered into the target bone in a concentration of between about 1 mg/ml and about 10 mg/ml.

In some embodiments, FGF is intraosseously administered into the target bone in an amount to provide a local tissue concentration of between about 0.1 mg/kg and about 10 mg/kg.

In some embodiments, the formulation comprises a hyaluronic acid carrier and bFGF. In some embodiments, formulations described in U.S. Pat. No. 5,942,499 ("Orquest") are selected as FGF-containing formulations.

In some embodiments, the bone forming agent comprises an effective amount of insulin-like growth factor. IGFs beneficially increase bone formation by promoting mitogenic activity and/or cell proliferation.

In some embodiments, the bone forming agent comprises an effective amount of parathyroid hormone (PTH). Without wishing to be tied to a theory, it is believed that PTH beneficially increases bone formation by mediating the proliferation of osteoblasts.

In some embodiments, the PTH is a fragment or variant, such as those taught in U.S. Pat. No. 5,510,370 (Hock) and U.S. Pat. No. 6,590,081 (Zhang), and published patent application 2002/0107200 (Chang), the entire contents of which are incorporated herein in their entirety. In one embodiment, the PTH is PTH (1-34) (teriparatide), e.g., FORTEO® (Eli Lilly and Company). In some embodiments, the BFA is a parathyroid hormone derivative, such as a parathyroid hormone mutein. Examples of parathyroid muteins are discussed in U.S. Pat. No. 5,856,138 (Fukuda), the entire contents of which are incorporated herein in its entirety.

In some embodiments, the bone forming agent comprises an effective amount of a statin. Without wishing to be tied to a theory, it is believed that statins beneficially increase bone formation by enhancing the expression of BMPs.

In some embodiments, the bone forming agent is a porous matrix, and is preferably injectable. In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 μm, for example, between about 50 and about 250 μm. In yet other embodiments of the present invention, in situ porosity is produced in the injected matrix to produce a porous scaffold in the injected fracture stabilizing cement. Once the in situ porosity is produced in the target tissue, the surgeon can inject other therapeutic compounds into the porosity, thereby treating the surrounding tissues and enhancing the remodeling process of the target tissue and the injectable cement.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the fragile OP body.

In another embodiment, the treatment is delivered via injectable absorbable or non-absorbable cement to the target tissue. The treatment is formulated using bioabsorbable macro-sphere technologies, such that it will allow the release of the bone forming agent first, followed by the release of the anti-resorptive agent. The cement will provide the initial stability required to treat pain in fractured target tissues. These tissues include, but are not limited to, hips, knee, vertebral body fractures and iliac crest fractures. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:
  a) a first formulation comprising an acid-soluble type I collagen solution (preferably between about 1 mg/ml and about 7 mg/ml collagen) and
  b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, photo- or nuclear. Suitable sources thereof include light, chemical reaction, enzymatically controlled reaction and an electric wire embedded in the material. To further elucidate the electric wire approach, a wire can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In one embodiment, the bone forming agent is a plurality of viable osteoprogenitor cells. Such viable cells, introduced into the bone, have the capability of at least partially repairing any bone loss experienced by the bone during the osteoporotic process. In some embodiments, these cells are introduced into the cancellous portion of the bone and ultimately produce new cancellous bone. In others, these cells are introduced into the cortical region and produce new cortical bone.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable cells are selected as an additional therapeutic agent or substance, the viable cells comprise mesenchymal stem cells (MSCs). MSCs provide a special advantage for administration into an uncoupled resorbing bone because it is believed that they can more readily survive the relatively harsh environment present in the uncoupled resorbing bone; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the bone are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the uncoupled resorbing bone.

Therefore, in accordance with the present invention, there is provided a kit for treating uncoupled resorbing bone, comprising:
a) a first formulation comprising a bone forming agent,
b) a second formulation comprising an anti-resorptive agent, and
c) a third formulation comprising viable cells.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

In some embodiments, the second formulation comprises an HSCA. In some embodiments, it comprises a drug pump. In some embodiments, the sustained release device comprises a bioresorbable material. The kit can further comprise an effective amount of a growth factor. In some embodiments, each sustained release device comprises microspheres.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-β or erythropoietin (EPO).

Accordingly, in some embodiments, the additional therapeutic agent is selected from the group consisting of viable cells and plasmid DNA.

The present invention is also directed to providing estrogen to the uncoupled resorbing bone. Therefore, in some embodiments, the second formulation comprises an effective amount of estrogen as an anti-resorptive.

These estrogen molecules serve to regulate the production of pro-inflammatory molecules such as TNF-α and certain interleukins.

It is believed that the elimination of estrogen is the primary cause of post-menopausal osteoporosis. Estrogen acts through high affinity receptors for osteoblasts and osteoclasts to regulate bone turnover. When this control is lost during menopause, bone resorption increases. Accordingly, re-establishing natural levels of estrogen in the post-menopausal bone should help re-establish more natural levels of osteoclasts.

Therefore, in accordance with another embodiment of the present invention, there is provided a method of treating OP, comprising intraosseously administering an effective amount of a formulation comprising estrogen into an uncoupled resorbing bone.

In some embodiments, the second formulation comprises an effective amount of Selective Estrogen Receptor Modulator ("SERM"). Without wishing to be tied to a theory, it is believed that a SERM binds with high affinity to estrogen receptors, but does so in a different manner than estrogen, and may regulate bone growth by mediating the upregulation of TGF-β.

In some embodiments, the SERM is selected from the group consisting of raloxifene, tamoxifen and droloxifene.

Biphosphonates (BP) are useful in treating uncoupled bone because they bind to the mineral portion of bone and are taken up by the osteoclasts. Once inside the osteoclast, they inhibit an enzyme essential to both osteoclast activity and survival.

In some embodiments, the BP is selected from the group consisting of alendronate, clodronate, EB-1053, etidronate, ibandronate, incadronate, neridronate, olpadronate, pamidronate, risedronate, tiludronate, YH-529 and zoledronate.

In some embodiments, the second formulation comprises an effective amount of calcitonin. Without wishing to be tied to a theory, it is believed that calcitonin binds to a G protein-coupled receptor in the osteoclast, and inhibits the osteoclast through both the calcium and cyclic AMP pathways.

In some embodiments, the second formulation comprises an effective amount of osteoprotegerin (OPG), a member of the tumor necrosis factor superfamily. Without wishing to be tied to a theory, it is believed that OPG binds RANK-ligand, a protein essential for osteoclast differentiation and development.

In addition, anti-cathepsins may also be used in accordance with the present invention. It is believed that inhibition of these enzymes inhibits the breakdown of the bone tissue. Preferably, the antagonists inhibit a cathepsin selected from the group consisting of cathepsin B, cathepsin L and cathepsin K.

In some embodiments, the second formulation comprises an effective amount of cathespin K inhibitor. Without wishing to be tied to a theory, it is believed that cathespin K is an enzyme considered essential for bone resorption.

It is further believed that intraosseous administration of an effective amount of a high specificity, anti-proliferative anti-resorptive agent in the second formulation would also help provide therapy to the patient having OP. It is believed that antiproliferative agents may have an effect on inflammation by affecting inflamed tissues which would limit the production of inflammatory cytokines. In some embodiments, the high specificity anti-proliferative is selected from the group consisting of a) rapamycin; b) an inhibitor of cyclin dependent kinase 9 (cdk); and c) Vitamin D analogs. In one embodiment, when rapamycin is selected, a dosage producing a local tissue concentration of between about 0.5 μg/kg and about 50 μg/kg is used.

Therefore, in accordance with another embodiment of the present invention, there is provided a method of treating OP, comprising intraosseously administering an effective amount of a formulation comprising a high specificity anti-proliferative agent into an uncoupled resorbing bone.

Rapamycin is a potent inhibitor of downstream signaling of TOR (target of Rapamycin) proteins. As such, it is responsible for coordinating the balance between protein synthesis and protein degradation. It is believed that OP is propagated by a loss of balance between bone regeneration and resorption. Since TOR proteins regulate multiple metabolic pathways, rapamycin may stabilize the balance of the cycle. Rapamycin may also directly affect the proliferation and subsequent immune reaction of osteocytes. In one embodiment, it is provided in a dose of about 0.1 μM to about 10 μM.

Cdk inhibitors may directly affect the proliferation and subsequent immune reaction of osteocytes. Exemplary cdk inhibitors include flavopiridol, roscovitine, and compounds disclosed in PCT Patent Publication No. WO 02/057240 (Lin), the specification of which is incorporated by reference herein in its entirety. In one embodiment, the cdk inhibitor is provided in an about 1 μM to about 10 μM dose.

In some embodiments, the Vitamin D analog is a VDR ligand, preferably 1 alpha 25 dihydroxyvitamin D3, a potent anti-proliferative.

The present invention is directed to providing directly into an uncoupled resorbing bone at least one highly specific cytokine antagonist (HSCA) or inhibitor capable of specifically inhibiting a cytokine (for example, a pro-inflammatory cytokine) present in the bone microenvironment. In one embodiment, the HSCA inhibits the action of a specific pro-inflammatory cytokine released by bone or bone marrow cells.

In some embodiments, the antagonist is capable of specifically inhibiting a pro-inflammatory cytokine selected from the group consisting of TNF-α, an interleukin (preferably, IL-1, Il-6 and IL-8), FAS, an FAS ligand, and IFN-gamma. Such specific inhibitors include those identified on pages 5-18 of U.S. Patent Publication No. U.S. 2003/0039651 ("Olmarker"), the specification of which is incorporated herein by reference in its entirety.

In some embodiments, the HSCA inhibits the cytokine by preventing its production. In some embodiments, the HSCA inhibits the cytokine by binding to a membrane-bound cytokine. In others, the HSCA inhibits the cytokine by binding to a solubilized, e.g. soluble, cytokine. In some embodiments, the HSCA inhibitor inhibits the cytokine by both binding to membrane-bound cytokines and binding to solubilized cytokines. In some embodiments, the HSCA is a monoclonal antibody ("mAb"). The use of mAbs is highly desirable since they bind specifically to a certain target protein and essentially to no other proteins. In some embodiments, the HSCA inhibits the cytokine by binding to a natural receptor of the target cytokine.

In some embodiments, the HSCA inhibits the cytokine by preventing its production. One example thereof is an inhibitor of p38 mitogen activated protein (MAP) kinase. In some embodiments, the TNF inhibitor inhibits the TNF by binding to membrane-bound TNF in order to prevent its release from membrane. In others, the TNF inhibitor inhibits the TNF by binding to solubilized TNF. One example thereof is etanercept. In some embodiments, the TNF inhibitor inhibits the TNF by both binding to membrane-bound TNF and to solubilized TNF. One example thereof is REMICADE® infliximab. In some embodiments, the HSCA inhibits the cytokine (e.g., TNF-α) by binding to a natural receptor of the target cytokine. In some embodiments, the TNF-α inhibitor is an inhibitor of TNF-α synthesis.

In some preferred embodiments, the anti-resorptive agent is a highly specific antagonist of tumor necrosis factor (TNF). These antagonists are highly preferred because the literature has shown that their administration into osteoporotic bone has the effect of restoring the osteoclast concentration in the bone to baseline (pre-osteoporotic) levels.

In particular, Kimble, R. B., et al., "Estrogen deficiency increases the ability of stromal cells to support murine osteoclastogenesis via an interleukin-1 and tumor necrosis factor-mediated stimulation of macrophage colony-stimulating factor production," J. Biol. Chem, 271(46): 18890-7 (1996), ("Kimble I") reported that both M-CSF and osteoclast concentrations return to essentially normal levels in ovariectomized rats that were administered an effective amount of an Il-1/TNF-α inhibitor. Kimble, R. B., et al., "The functional block of TNF but not of IL-6 prevents bone loss in ovariectomized mice," J Bone Min. Res., 12(6) 935-941 (1997), (Kimble II") reported that osteoclast concentrations return to essentially normal levels in ovariectomized mice that were administered an effective amount of a TNF-α inhibitor, and further conclude that the estrogen-regulated cytokine that plays a central role in the mechanism by which estrogen deficiency causes bone loss is not IL-6, but rather TNF.

Accordingly, since these TNF antagonists do not destroy osteoclast production or function, but merely have the effect of returning osteoclast levels to their normal levels, they are highly preferred.

Preferred TNF antagonists include, but are not limited to, the following: etanercept (ENBREL®, Amgen); infliximab (REMICADE®, Johnson and Johnson); D2E7, a human anti-TNF monoclonal antibody (Knoll Pharmaceuticals, Abbott Laboratories); CDP 571 (a humanized anti-TNF IgG4 antibody) and CDP 870 (an anti-TNF alpha humanized monoclonal antibody fragment), both from Celltech; soluble TNF receptor Type I (Amgen); pegylated soluble TNF receptor Type I (PEGs TNF-R1) (Amgen); and onercept, a recombinant TNF binding protein (r-TBP-1) (Serono).

TNF antagonists suitable for compositions, combination therapy, co-administration, devices and/or methods of the present invention (optionally further comprising at least one antibody, specified portion and/or variant thereof, of the present invention), include, but are not limited to, a TNF chemical or protein antagonist, anti-TNF antibodies, a TNF monoclonal or polyclonal antibody or fragment, a soluble TNF receptor (e.g., p55, p70 or p85) or fragment, fusion polypeptides thereof, a small molecule TNF antagonist such as TNF binding protein I or II (TBP-1 or TBP-II), nerelimonmab, REMICADE® infliximab, etanercept (ENBREL®), adalimulab (HUMIRA™), CDP-571, CDP-870, afelimomab, lenercept and the like, antigen-binding fragments thereof, and receptor molecules which bind specifically to TNF; compounds which prevent and/or inhibit TNF synthesis, TNF release or its action on target cells, such as thalidomide, tenidap, and phosphodiesterase inhibitors (e.g. pentoxifylline and rolipram); A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

In one embodiment, the TNA antagonist is a cycline compound. Cycline compounds inhibit TNF-α in a non-specific manner. TNF-α and other similar bioactive substances are first produced in an inactive form and transported to the cell membrane. Upon activation, the active part of the pro-TNF-α is cleaved and released. This process is called shedding and may be initiated by one or more enzymes. These enzymes all have in common a metal ion and are called matrix metalloproteinases (MMPs). Cycline compounds are known to bind to metal ions and will thereby inhibit the action of the MMP and subsequently the release of TNF-α and other pro-inflammatory cytokines in a non-specific manner. In some embodiments, the cycline compound is selected from the group consisting of doxycycline, lymecycline, oxicycline compound, tetracycline, minocycline, chemically modified tetracycline (CMT) and KB-R7785.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNF-alpha (TNFα). A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

The chimeric antibody cA2 comprises the antigen binding variable region of the high-specificity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the specificity constant of chimeric antibody cA2 was calculated to be $1.04 \times 10^{10} M^{-1}$. Preferred methods for determining monoclonal antibody specificity and specificity by competitive inhibition can be found in Harlow et al., *Antibodies: A Laboratory Manual*, Cold Spring Harbor Laboratory Press, Cold Spring Harbor, N.Y. (1988); Colligan et al., eds.; *Current Protocols in Immunology*, (NY: Greene Publishing Assoc. and Wiley Interscience) (1992-2000); Kozbor et al., *Immunol. Today*, 4:72-79 (1983); and Ausubel et al., eds. *Current Protocols in Molecular Biology*, (NY: Wiley Interscience) (1987-2000); and Muller, R., "Determination of affinity and specificity of anti-hapten antibodies by competitive radioimmunoassay," *Meth. Enzymol.*, 92: 589-601 (1983), which are entirely incorporated herein by reference.

In a particular embodiment, murine monoclonal antibody A2 is produced by a cell line designated c134A. Chimeric antibody cA2 is produced by a cell line designated c168A. cA2 is described in detail in U.S. Pat. No. 6,284,471 (Le et al.) which is incorporated by reference herein in its entirety.

Additional examples of monoclonal anti-TNF antibodies that can be used in the present invention are described in the art (see, e.g., U.S. Pat. No. 5,231,024; Möller, A., et al., "Monoclonal antibodies to human tumor necrosis factor alpha: in vitro and in vivo application," *A. et al., Cytokine* 2(3): 162-169 (1990); U.S. Pat. No. 6,277,969; Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (published Oct. 26, 1988); Liang, C. M., et al., "Production and characterization of monoclonal antibodies against recombinant human tumor necrosis factor/cachectin," *Biochem. Biophys. Res. Comm.*, 137: 847-854 (1986); Meager, A., et al., "Preparation and characterization of monoclonal antibodies directed against antigenic determinants of recombinant human tumour necrosis factor (rTNF)," *Hybridoma*, 6: 305-311 (1987); Fendly, B. M., et al., "Murine monoclonal antibodies defining neutralizing epitopes on tumor necrosis factor," *Hybridoma*, 6: 359-369 (1987); Bringman, T. S., et al., "Monoclonal antibodies to human tumor necrosis factors alpha and beta: application for affinity purification, immunoassays, and as structural probes," *Hybridoma*, 6: 489-507 (1987); and Hirai, M., et al., "Production and characterization of monoclonal antibodies to human tumor necrosis factor," *J. Immunol. Meth.*, 96: 57-62 (1987), which references are entirely incorporated herein by reference).

Preferred TNF receptor molecules useful in the present invention include those that bind TNFα with high specificity (see, e.g., Feldmann et al., International Publication No. WO 92/07076 (published Apr. 30, 1992); Schall, T. J. et al., "Molecular cloning and expression of a receptor for human tumor necrosis factor," *Cell*, 61: 361-370 (1990); and Loetscher, H. et al., "Molecular cloning and expression of the human 55 kd tumor necrosis factor receptor," *Cell*, 61: 351-359 (1990), which are entirely incorporated herein by reference) and, optionally, possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran, A. E. et al., "Characterization of ligand binding by the human p55 tumour-necrosis-factor receptor. Involvement of individual cysteine-rich repeats," *Eur. J. Biochem.*, 223: 831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., "Two tumor necrosis factor-binding proteins purified from human urine. Evidence for immunological cross-reactivity with cell surface tumor necrosis factor receptors," *J. Biol. Chem.*, 265:, 1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high specificity, as well as other undefined properties, can contribute to the therapeutic results achieved.

TNF receptor multimeric molecules useful in the present invention can comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule.

TNF immunoreceptor fusion molecules useful in the methods and compositions of the present invention can comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer, W. et al., "Recombinant soluble tumor necrosis factor receptor proteins protect mice from lipopolysaccharide-induced lethality," *Eur. J. Immunol*, 21: 2883-2886 (1991); Ashkenazi, A., et al., "Protection against endotoxic shock by a tumor necrosis factor receptor immunoadhesin," *Proc. Natl. Acad. Sci. USA*, 88: 10535-10539 (1991); Peppel, K. et al., "A tumor necrosis factor (TNF) receptor-IgG heavy chain chimeric protein as a bivalent antagonist of TNF activity," *J. Exp. Med.*, 174: 1483-1489 (1991); Kolls, J. et al., "Prolonged and effective blockade of tumor necrosis factor activity through adenovirus-mediated gene transfer," *Proc. Natl. Acad. Sci. USA*, 91: 215-219 (1994); Butler, D. M. et al., "TNF receptor fusion proteins are effective inhibitors of TNF-mediated cytotoxicity on human KYM-1D4 rhabdomyosarcoma cells," *Cytokine*, 6(6): 616-623 (1994); Baker, D. et al., "Control of established experimental allergic encephalomyelitis by inhibition of tumor necrosis factor (TNF) activity within the central nervous system using monoclonal antibodies and TNF receptor-immunoglobulin fusion proteins," *Eur. J. Immunol.*, 24: 2040-2048 (1994); and Beutler et al., U.S. Pat. No. 5,447,851, each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon, D. J. et al., "Designing CD4 immunoadhesins for AIDS therapy," *Nature*, 337: 525-531 (1989), which references are entirely incorporated herein by reference.

A functional equivalent, derivative, fragment or region of a TNF receptor molecule refers to a protein or peptide which comprises a portion of the TNF receptor molecule, or the portion of the TNF receptor molecule nucleic acid sequence which encodes the TNF receptor molecule, that is of sufficient size and sequences to functionally resemble a TNF receptor molecule that can be used in the present invention (e.g., binds TNFα with high specificity and possesses low immunogenicity). A functional equivalent of a TNF receptor molecule also includes a modified TNF receptor molecule that functionally resembles a TNF receptor molecule that can be used in the present invention (e.g., binds TNFα with high specificity and possesses low immunogenicity). For example, a functional equivalent of a TNF receptor molecule can contain a "silent" codon or one or more amino acid substitutions, deletions or additions (e.g., substitution of one acidic amino acid for another acidic amino acid; or substitution of one codon encoding the same or a different hydrophobic amino acid for another codon encoding a hydrophobic amino acid). See Ausubel et al., *Current Protocols in Molecular Biology* (NY: Greene Publishing Assoc. and Wiley-Interscience) (1987-2003).

In some embodiments, the monoclonal antibody that inhibits TNF-α is selected from the group consisting of monoclonal rodent-human antibodies, rodent antibodies, human antibodies or any portion or portions thereof, having at least one antigen binding region of an immunoglobulin variable region, which antibody binds TNF. Preferably, this monoclonal antibody is selected from the group of compounds disclosed in U.S. Pat. No. 6,277,969, the specification of which is entirely incorporated herein by reference. In some embodiments, REMICADE® infliximab is delivered in a formulation having an infliximab concentration of between about 0.4 mg/ml and about 4 mg/ml.

In some embodiments, the specific inhibitor of TNF-α is an inhibitor of p38 MAP kinase, preferably, a small molecule inhibitor of p38 MAP kinase. The inhibition of p38 MAP kinase is believed to block production of both TNF-α and Il-2, both of which are pro-inflammatory cytokines. The small molecule inhibitors of p38 MAP kinase are very specific & potent (~nM). Without wishing to be tied to a theory, it is believed that inhibition of p38 should not block TGF signaling nor TGF activity. It is further believed that p38 inhibitors may also block induction of some metalloproteinases, COX 2 and NO synthetase. It is further believed that P38 inhibitors do not inhibit interleukins involved in immune cell proliferation such as IL-2.

Intraosseous administration of an effective amount of a high specificity antagonist (HSA) of p38 kinase would also help provide therapy to a patient having OP. It is believed that the p38 kinase site regulates the production of TNF-α, IL-1 and COX-2 enzyme.

Therefore, in accordance with another embodiment of the present invention, there is provided a method of treating OP, comprising locally intraosseously administering an effective amount of a formulation comprising a high specificity antagonist of p38 kinase into an OP bone.

Preferably, they are provided in an about 10 nM to about 10 uM dose. Some high specificity antagonists of p38 kinase are disclosed in Zhang, C., "Mitogen-activated protein (MAP) kinase regulates production of tumor necrosis factor-alpha and release of arachidonic acid in mast cells. Indications of communication between p38 and p42 MAP kinases," *J. Biol. Chem.*, 272(20): 13397-402 (1997); Pargellis, C., "Inhibition of p38 MAP kinase by utilizing a novel allosteric binding site," *Nature Structural Biology*, 9(4): 268-272 (2002); and Chae, H. J., "The p38 mitogen-activated protein kinase pathway regulates interleukin-6 synthesis in response to tumor necrosis factor in osteoblasts," *Bone*, 28(1): 45-53 (2001), and in U.S. Pat. No. 6,541,477 ("Goehring") and U.S. Pat. No. 5,965,583 ("Beers"), the specifications of which are herein incorporated by reference in their entirety. Preferably, the HSA of p38 kinase is administered in a dosage to produce a local tissue concentration of between about 5 µg/kg and about 50 µg/kg.

In some embodiments, the p38 kinase inhibitor is selected from the group consisting of:
  a) diaryl imidizole;
  b) N,N'-diaryl urea (developed by Bayer, Boehringer Ingelheim and Vertex);
  c) N,N-diaryl urea (developed by Vertex);
  d) benzophenone (developed by Leo Pharmaceuticals);
  e) pyrazole ketone (developed by Hoffman-LaRoche);
  f) indole amide (developed by GlaxoSmithKline and Scios);
  g) diamides (developed by AstraZeneca);
  h) quinazoline (developed by GlaxoSmithKline);
  i) pyrimido [4,5-d]pyrimidinone (developed by GlaxoSmithKline and Hoffman LaRoche); and
  j) pyridylamino-quinazolines (developed by Scios).

Members of this group are described, for example, in Zhang et al., supra, Pargellis et al., supra, Chae et al., supra, Cirillo, P. F. et al., "The non-diaryl heterocycle classes of p38 MAP kinase inhibitors," *Current Topics in Medicinal Chemistry*, 2: 1021-1035 (2002), Boehm et al, *Exp. Opin. Ther. Patents*, 10(1): 25-38 (2000), and Lee, J. C. et al., "Inhibition of p38 MAP kinase as a therapeutic strategy," *Immunopharmacology*, 47: 185-2001 (2000).

In some embodiments, the p38 kinase inhibitor is selected from the group consisting of SK&F 86002; SB 203580; L-167307; HEP 689; SB220025; VX-745; SU4984; RWJ 68354; ZM336372; PD098059; SB235699; and SB220025.

In some embodiments, the p38 kinase inhibitor is characterized as a 1-aryl-2-pyridinyl heterocycle. In some embodiments, the 1-aryl-2-pyridinyl heterocycle is selected from the group consisting of:
  a) 4,5 substituted imidazole,
  b) 1,4,5 substituted imidizole;
  c) 2,4,5 substituted imidizole;
  d) 1,2,4,5 substituted imidizole; and
  e) non-imidizole 5-membered ring heterocycle.

In some embodiments, the p38 kinase inhibitor has at least 3 cyclic groups.

In some embodiments, the p38 kinase inhibitor is selected from the group consisting of a molecule that is readily soluble in water and a substantially water-insoluble molecule. In some embodiments, the highly specific antagonist is a p38 kinase inhibitor that is a substantially water-insoluble molecule. The substantially water insoluble p38 inhibitor may be advantageous in that, if injected into the uncoupled resorbing bone, it will remain in the bone as a solid and will only slightly solubize over time, thereby providing sustained release.

In some embodiments, the HSCA is a specific antagonist (i.e., inhibitor) of an interleukin. Preferably, the target interleukin is selected from the group consisting IL-1, IL-2, IL-6, IL-8, IL-1β and IL-12. Preferred antagonists include, but are not limited to, Kineretg (recombinant IL 1-RA, Amgen), IL1-Receptor Type 2 (Amgen) and IL-1 Trap (Regeneron).

Since it is known that many pro-inflammatory proteins play a role in osteoporosis, and that the antagonists of the present invention are highly specific, it is further believed that injecting at least two of the highly specific antagonists of the present invention directly into the bone would be even more advantageous in certain embodiments.

Therefore, in accordance with the present invention, there is provided a method of treating an osteoporotic bone, comprising administering a formulation comprising at least two highly specific antagonists of pro-inflammatory cytokines selected from the group consisting of TNF-α, an interleukin (preferably, IL-1, Il-6 and IL-8), FAS, an FAS ligand and IFN-gamma into the bone.

In one embodiment, at least one of the substances is an antagonist of TNF-α. In one embodiment, the other substance is an antagonist of an interleukin.

BFAs and ARAs of the present invention can be administered either as individual therapeutic agents or in combination with other therapeutic agents. They can be administered alone or with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. In one embodiment, about 1.0 to 5, and preferably about 1 to 10 milligrams per kilogram per day given in divided doses 1 to 6 times a day or in sustained release form is effective to obtain desired results.

In some embodiments, agents can be administered in a dosage of about 0.1 to about 100 mg/kg, such as about 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4, or 2 hours, or any combination thereof. In one embodiment, the agents are administered three times in one month, e.g. three times in the first month.

In some embodiments, dosage forms (composition) suitable for internal administration generally contain from about 0.1 milligram to about 500 milligrams of active ingredient per unit. In these pharmaceutical compositions, the active ingredient will ordinarily be present in an amount of about 0.5-95% by weight based on the total weight of the composition.

In some embodiments, agents can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques. Suitable pharmaceutical carriers are described in the most recent edition of Remington's Pharmaceutical Sciences, A. Osol, a standard reference text in this field of art.

Because osteoporosis ("OP") involves the progressive resorption of bone in which many factors are involved, in many instances, simply providing a single dose or even a regimen over the space of a few days may not be sufficient to manage the OP. Therefore, there is a need to provide a long-term drug therapy treatment of OP that does not require multiple injections. Accordingly, it is desirable for the AR and/or BF agent to remain within the bone as long as possible in a pharmaceutically effective amount. The half-life of the AR and/or BF agent within the bone will depend upon many factors, including the size of the AR and/or BF agent and its charge. In general, the larger the molecular weight of the AR and/or BF agent, the more likely it is to remain contained by the bone.

When selecting an AR and/or BF agent with a relatively short half-life (residence time) in the bone, it would be desirable for a relatively large dose of the AR and/or BF agent to be administered into the bone. In this condition, the residence time of the AR and/or BF agent would not cause the AR and/or BF agent to fall below therapeutically effective concentrations until an extended period of time has elapsed.

When injecting formulations into the bone, it is desirable that the volume of drug delivered be no more than about 10 ml, for example, no more than about 5 ml, (i.e., a maximum of about 5 ml) for example, between about 1 and about 3 ml.

As noted above, continuous delivery of the AR and/or BF agent is considered to be highly advantageous. Accordingly, in some embodiments, at least the BF and/or AR agent is provided in a sustained release (i.e., delivery) device. The sustained release device is adapted to remain within the bone for a prolonged period and slowly release the BF and/or AR agent contained therein to the surrounding environment. This mode of delivery allows a BF and/or AR agent to remain in therapeutically effective amounts within the bone for a prolonged period. One or more additional therapeutic agents can also be delivered by a sustained delivery device.

In some embodiments, the BF and/or AR agent is predominantly released from the sustained delivery device by its diffusion through the sustained delivery device (for example, through a polymer or a porous ceramic such as hydroxyapatite). In others, the BF and/or AR agent is predominantly released from the sustained delivery device by the biodegradation of the sustained delivery device (for example, biodegradation of a polymer or a porous ceramic such as hydroxyapatite). In others, the BF and/or AR agent is predominantly released from the sustained delivery device by convection, such as through a drug pump.

In some embodiments, the sustained release device (i.e., sustained delivery device) comprises a bioresorbable material whose gradual erosion causes the gradual release of the BF and/or AR agent to the bone environment. In some embodiments, the sustained release device comprises a bioresorbable polymer. In one embodiment, the bioresorbable polymer has a half-life of at least one month, for example, at least two months, e.g., at least 6 months.

In some embodiments, the sustained release device provides continuous release. In others, it provides intermittent release. In others, the sustained release device comprises a biosensor. Other release modes may also be used.

In some embodiments, the sustained delivery device comprises a plurality of bioerodable macrospheres. In some embodiments, the BF and/or AR agent is preferably contained in a gelatin (or water or other solvent) within the capsule, and is released to the bone environment when the outer shell of the capsule has been eroded. The device can include a plurality of capsules having outer shells of varying thickness, so that the sequential breakdown of the outer shells provides periodic release of the BF and/or AR agent.

In some embodiments, the sustained delivery device comprises a plurality (e.g., at least one hundred) of water-containing chambers, each chamber containing the BF and/or AR agent. Each chamber is defined by bilayer lipid membranes comprising synthetic duplicates of naturally occurring lipids. The release of the drug can be controlled by varying at least one of the aqueous excipients, the lipid components, and the manufacturing parameters. In one embodiment, the formulation comprises no more than 10% lipid. In some embodiments, the DEPOFOAM™ technology of Skyepharma PLC (London, United Kingdom) is selected.

In some embodiments, the sustained delivery device comprises a delivery system disclosed in U.S. Pat. No. 5,270,300 ("Hunziker"), the specification of which is incorporated herein by reference in its entirety.

In some embodiments, the sustained delivery device comprises a liposomal delivery system, such as that disclosed in WO 03/000190. Liposomes are small spheres whose walls are layers of lipids with water. As they form, liposomes entrap water and any water soluble solutes that are present. Because of this entrapping ability, they are useful as delivery systems. For the purposes of the present invention, a preferred embodiment includes the use of a multilamellar vesicle, and any naturally occurring phospholipid, such as dipalmitoylphosphatidylcholine (DPPC).

A liposome may be a vesicle having at least one lipid bilayer surrounding an inner liquid phase (a lipid bilayer surrounding either a liquid core or a liquid phase dispersed between it and another lipid bilayer). The liposome may have various structures such as multilamellar (MLVs), unilamellar (ULVs) and paucilamellar (PLVs) vesicles. The resulting structure of the liposome is dependent, in part, on the choice of materials forming the hydrophobic phase and the manufacturing parameters, such as temperature and incubation time.

Some liposomes comprise at least one amphiphilic bilayer-forming substance. The therapeutic substances contained therein may be contained either within the lipid bilayer or the hydrophilic compartments of the liposome. The amphiphilic bilayer-forming substance comprises both a hydrophilic and a lipophilic group and is capable of forming, either alone or in combination with other lipids, the bilayer of a liposome. The lipid can have single or multiple lipophilic side chains being either saturated or unsaturated in nature and branched or linear in structure. The amphiphilic bilayer-forming substance can be a phospoholipid or a ceramide.

In some embodiments, the sustained delivery device comprises the co-polymer poly-DL-lactide-co-glycolide (PLG). Preferably, the formulation is manufactured by combining the BF and/or AR agent, the co-polymer and a solvent to form a droplet, and then evaporating the solvent to form a microsphere. The plurality of microspheres are then combined in a biocompatible diluent. Preferably, the BF and/or AR agent is released from the co-polymer by its diffusion therethrough and by the biodegradation of the co-polymer. In some embodiments hereof, the PROLEASE® technology of Alkermes (Cambridge, Mass.) is selected.

In some embodiments, the sustained delivery device comprises a hydrogel. Hydrogels can also be used to deliver the BF and/or AR agent in a time-release manner to the disc environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the BF and/or AR agent at the application site, thereby eliminating undesired migration from the bone. The hydrogels are also biocompatible, e.g., not toxic, to cells suspended in the hydrogel.

A "hydrogel-BF and/or AR agent composition" is a suspension of a hydrogel-containing desired agent. The hydrogel-BF and/or AR agent composition forms a uniform distribution of BF and/or AR agent with a well-defined and precisely controllable density. Moreover, the hydrogel can support very large densities of BF and/or AR agent.

Hydrogels suitable for use in the present invention include water-containing gels, i.e., polymers characterized by hydrophilicity and insolubility in water. See, for instance, "Hydrogels", In *Concise Encyclopedia of Polymer Science and Engineering*, Mark et al., eds. (Wiley and Sons) pp. 458-459 (1990), the disclosure of which is incorporated herein entirely by reference in its entirety. Although their use is optional in the present invention, the inclusion of hydrogels can be highly advantageous since they tend to contribute a number of desirable qualities. By virtue of their hydrophilic, water-containing nature, hydrogels can:

a) house viable cells, such as mesenchymal stem cells and
b) assist with load bearing capabilities of the bone.

In one embodiment, the hydrogel is a fine, powdery synthetic hydrogel. The hydrogel can include one or more of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly (vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine) and poly(vinyl imidazole).

In some embodiments, the sustained delivery device includes a polymer selected from the group consisting of PLA, PGA, PCL and mixtures thereof.

When the sustained delivery vehicle is essentially a depot, preferably, the formulation of the present invention is injected into the bone through a small bore needle. In some embodiments, the needle has a bore of about 22 gauge or less, so that the possibilities of producing tissue damage are mitigated. For example, the needle can have a bore of about 24 gauge or a smaller bore, so that the possibilities of producing tissue damage are even further mitigated.

Accordingly, in another aspect of the present invention, there is provided a kit for treating an osteoporotic bone, comprising:

a) a first formulation comprising a bone forming agent,
b) a second formulation comprising an effective amount of an anti-resorptive agent, and
c) a sustained release device adapted to deliver the second formulation into the bone.

Accordingly, in another aspect of the present invention, there is provided a kit for treating
   a) a first formulation comprising an effective amount of a bone-forming agent,
   b) a first sustained release device adapted to deliver the first formulation into the bone,
   c) a second formulation comprising an effective amount of an anti-resorptive agent, and
   d) a second sustained release device adapted to deliver the second formulation into the bone.

In some embodiments, the bone forming agent is an osteoconductive material, an anabolic agent, a growth factor (such as BMP or FGF). In some embodiments, the second sustained release device comprises a drug pump. In some embodiments, it comprises bioresorbable materials. The kits can also encompass an effective amount of a growth factor.

When selecting an BF and/or AR agent with a relatively long half-life, it may be assumed that a relatively small dose of the BF and/or AR agent can be administered into the bone. In this condition, the slow depletion of the BF and/or AR agent would not cause the BF and/or AR agent to fall below therapeutically effective levels in the bone until an extended period of time has elapsed.

In some embodiments in which BF and/or AR agents have long half-lives within the bone, the dose administered can be very small.

For example, if it is believed that a BF and/or AR agent is effective when present in the range of about 1-10 mg/kg or 1-10 ppm (as is believed to be the case for the TNF antagonist REMICADE® infliximab as an AR agent), and since the cancellous portion of a cervical vertebral body has a volume of about 3 ml (or 3 cc or 3 g), then only about 3-30 μg of the HSCA would need be administered to the bone in order to provide a long lasting effective amount of the drug. The small amounts available by this route reduce the chances of deleterious side effects of the BF and/or AR agent.

For example, suppose a clinician administered 0.3 ml of 60 mg/ml REMICADE® infliximab into a 2.7 cc bone, thereby producing an infliximab concentration in the bone of about 6 mg/ml, or 6 parts per thousand. Without wishing to be tied to a theory, if infliximab has the same half-life within a bone as it does when administered systemically (i.e., about 1 week), then the concentration of infliximab would remain above about 10 ppm for about 9 weeks. Therefore, if another dose were needed, the clinician would only need to provide the second dose after about two months.

Therefore, in some embodiments, the BF and/or AR agent is provided in a dose of less than about 1 mg, for example, a maximum of about 0.5 mg, e.g., less than about 0.5 mg, e.g., less than about 0.1 mg, e.g., less than about 0.01 mg, e.g., less than about 0.001 mg. The smaller amounts available by this route reduce the chances of deleterious side effects of the BF and/or AR agent. Preferably, the BF and/or AR agent provided in these smaller amounts is a TNF antagonist, more preferably it is REMICADE® infliximab. In some embodiments, the formulation is administered in an amount effective to reduce osteoclast production. In some embodiments, the formulation is administered in an amount effective to maintain the bone mineral density of the target bone. In some embodiments, the formulation is administered in an amount effective to increase the bone mineral density of the target bone.

In accordance with one aspect of the invention, the BF agent, the AR agent and an additional (e.g., third) therapeutic agent(s) are locally administered into the bone. More than one additional therapeutic agent can be administered. For example, there can be fourth, fifth and sixth therapeutic agents.

In some embodiments, the BF agent, AR agent and additional therapeutic agent(s) are administered simultaneously. In others, the BF agent is administered first. In some embodiments, the AR agent is administered after the BF agent has been depleted.

Examples of other (additional) therapeutic agents include, but are not limited to: vitamins and other nutritional supplements; hormones; glycoproteins; fibronectin; peptides and proteins; carbohydrates (both simple and/or complex); proteoglycans; oligonucleotides (sense and/or antisense DNA and/or RNA); demineralized bone matrix; antibodies (for example, to infectious agents, tumors, drugs or hormones); gene therapy reagents; and anti-cancer agents. Genetically altered cells and/or other cells may also be included in a matrix of this invention. If desired, substances such as pain killers and narcotics may also be admixed with a polymer for delivery and release to the bone.

In some embodiments particularly suited for cancer patients, an anti-cancer drug is locally administered.

In some embodiments particularly suited for patients having a fracture, an antibiotic is locally administered for infection control.

In some embodiments, the formulation includes a radioopaque agent so that the injected material can be fluoroscopically monitored.

In some embodiments, the formulation comprises a suitable biocompatible solvent such as saline. In some embodiments, the solvent is selected from the solvents disclosed in U.S. Pat. No. 6,277,969, the specification of which is incorporated herein by reference in its entirety. In some embodiments, the solvent is preferably selected from the group consisting of dimethyl sulfoxide (DMSO) and ethanol.

It would be useful for the clinician to first perform a diagnostic test in order to confirm that the targeted bone is, in fact, osteoporotic or osteopenic prior to providing the injection. This is typically done through a DEXA (Dual X-Ray Absorptiometer) analysis.

In some embodiments, post-delivery monitoring or tracking is used to assess bone density and growth.

It is believed that intraosseous administration of an effective amount of a high specificity antagonist of the NO synthase enzyme would also help provide therapy to the patient having OP. It is believed that the NO synthase enzyme regulates the production of NO, which is known to have pro-inflammatory effects.

Therefore, in accordance with another embodiment of the present invention, there is provided a method of treating OP, comprising intraosseously administering an effective amount of a formulation comprising a high specificity antagonist of NO synthase into an uncoupled resorbing bone.

Examples of high specificity antagonists include NO synthase are N-iminoethyl-L-lysine (L-NIL), and $N^G$-monomethyl-L-arginine.

In some embodiments, the high specificity antagonists of NO synthase may be administered systemically.

The present invention is also directed to providing a highly specific anti-apoptosis molecule to the uncoupled resorbing bone. These molecules serve to protect against osteocyte apoptosis. Preferred compounds include EPO, erythropoetin mimetic peptides, EPO mimetibodies, IGF-I, IGF-II and caspase inhibitors.

Therefore, in accordance with another embodiment of the present invention, there is provided a method of treating OP, comprising intraosseously administering an effective amount of a formulation comprising a high specificity anti-apoptotic agent into an uncoupled resorbing bone.

In addition, non-steroidal anti-inflammatory drugs (NSAIDs) may also be selected as an additional, e.g., a second, therapeutic agent. In some embodiments, the NSAID is anabolic, and is, for example, selected from the group consisting of TOLMETIN™ (available from Ortho-MacNeil), SUPROL™ (available from Johnson & Johnson), and Tiaprofenic acid (available from Roussel Labs). Preferably, the anabolic NSAID is administered in a dosage sufficient to produce an initial local tissue concentration of between about 5 µg/kg and about 500 µg/kg. In some embodiments, the NSAID is a dual inhibitor of both the COX and LOX pathways, and is preferably TEPOXALIN™ (available from Johnson & Johnson).

As noted above, local treatment of osteoporosis requires the sustained presence of the anti-resorptive agent within a very vascular bony tissue. Accordingly, it appears that providing a slow, continuous release of the anti-resorptive into the bony tissue would insure the sustained presence of the anti-resorptive agent.

Therefore, in some embodiments, there is provided a device for providing sustained delivery of a therapeutic agent into a bone, for example, a device comprising:
   a) a chamber for housing an anti-resorptive agent,
   b) an exit port in fluid communication with the chamber,
   c) an effective amount of an anti-resorptive agent housed within the chamber, and
   d) means for expelling the anti-resorptive agent from the chamber through the exit port.

In some embodiments, the device comprises a formulation (e.g., a first formulation) comprising an effective amount of the anti-resorptive agent housed within the chamber.

Figure 7:
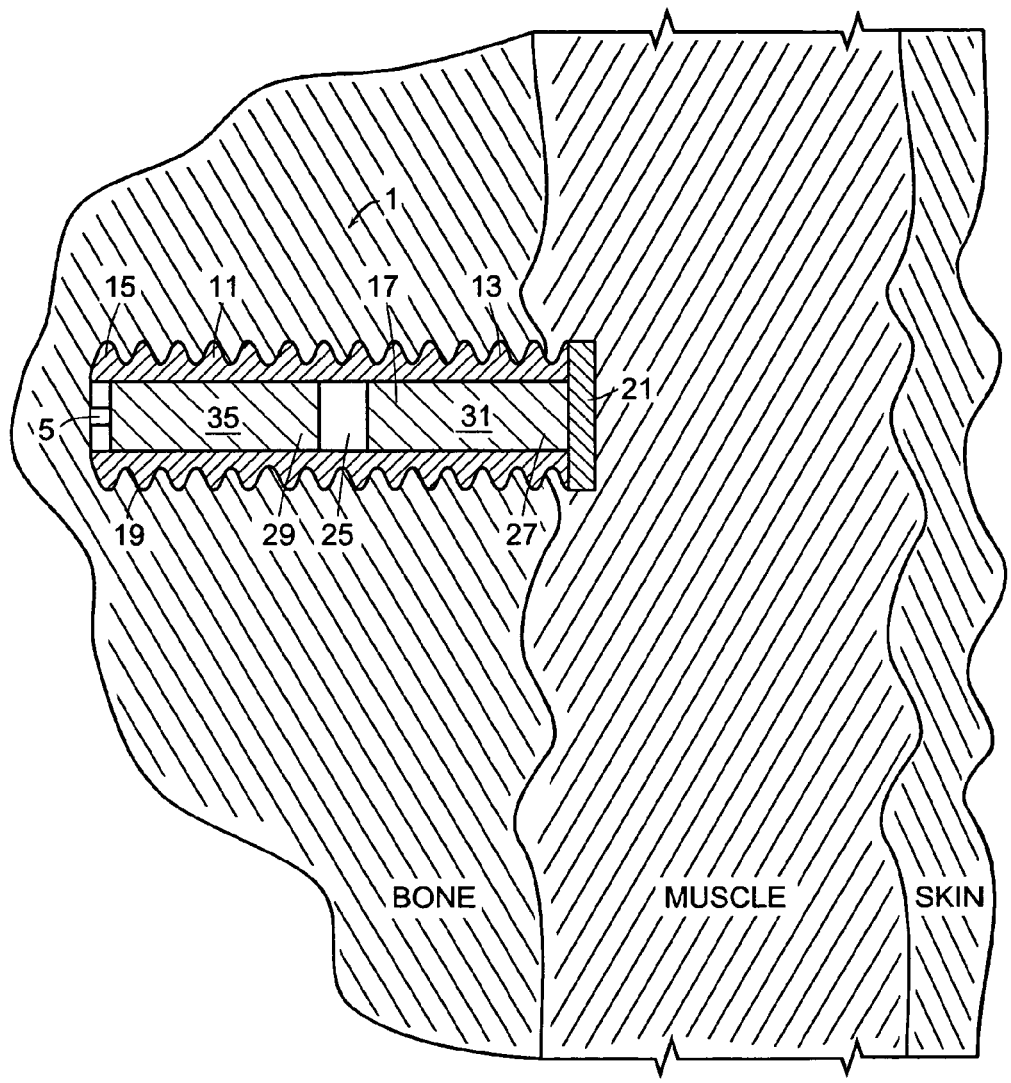
FIG. 7 is a cross-section of an osmotic drug pump implant of the present invention.

Now referring to FIG. 7, there is provided an osmotic pump implant 1 for providing sustained delivery of a therapeutic agent into a bone. In this embodiment, the osmotic pump implant comprises:
   a) a tubular member 11 including a proximal end portion 13, a distal end portion 15 and a throughbore 17,
   b) a semi-permeable membrane 21 located in the proximal end portion of the tubular member,
   c) a piston 25 provided in the tubular member, defining a proximal chamber 27 and a distal chamber 29,
   d) an osmotic engine 31 located in the proximal chamber, and
   e) a therapeutic drug 35 located in the distal chamber,
wherein the tubular member has an outer surface adapted to anchor to the bone, for example, an outer surface having a fastening means 19 (e.g., a threadform) thereon.

In some embodiments, the tubular member has an outer surface which has a hook thereon. In some embodiments, the outer surface has a porosity effective for inducing bone growth, such as a porosity with an average pore size of between about 20 µm and about 500 µm.

The device shown in FIG. 7 works upon the following principle. Water infiltrates the semi-permeable membrane and is imbibed in the osmotic engine. Upon the receipt of water, the material selected for the osmotic engine swells. Since the semi-permable membrane is fixed and the piston is axially movable, the force produced by the swelling of the osmotic engine forces the piston to slide distally. This movement in turn forces the drug out the distal exit port 5. In some embodiments, design features of the device are adopted from U.S. Pat. No. 5,728,396 ("Peery"), the specification of which is incorporated by reference in its entirety.

In some embodiments, the therapeutic drug provided in FIG. 7 is an anti-resorptive (AR) agent. In some embodiments, the device is tailored to provide the AR agent in an amount of at least 70% of the predetermined therapeutic level for at least about six (6) months. In some embodiments, the therapeutic drug provided is a bone forming agent, such as a growth factor (e.g., BMP or a FGF).

A major impediment to many osmotic engine-based delivery devices is the start-up time. In effect, the osmotic engine must be primed before the therapeutic drug is eluted from the distal end of the device. However, since Lane, supra, has demonstrated that the anti-resorptive agent need not be present during the initial bone-growth process, the device need not provide the AR agent for that initial period. Rather the device may deliver the AR agent after a lead time of at least 15 days and still provide therapy.

Because the bone is a very vascular tissue (and especially so in many osteoporotic patients), it may be that the vascularity also drains the locally administered bone forming agent (BF agent) quickly. For example, it is reasonable to expect BF agent levels to be essentially depleted within about 10-15 days of their local administration. Since in the case of many BF agents, it may be advantageous to provide an effective amount of the BF agent within the bone for a longer duration, there appears to be a need for a device that insures the continuous presence of the BF agent for an indefinite period.

Figure 8:
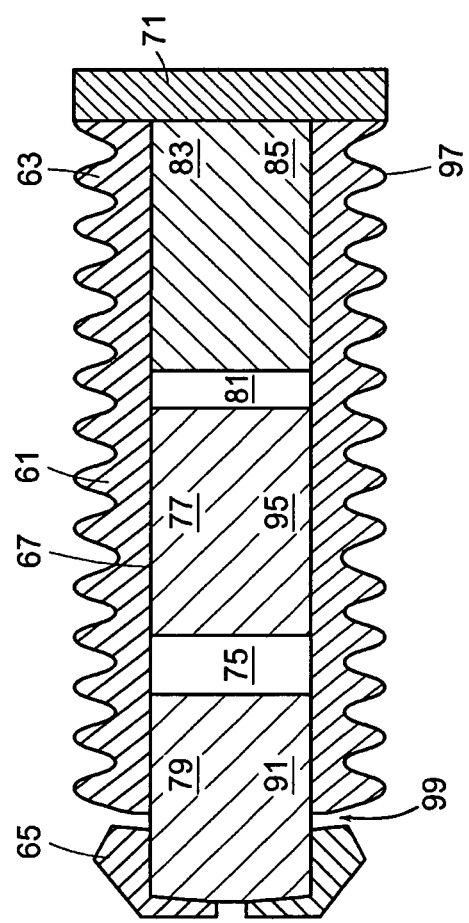
FIG. 8 is a cross-section of an osmotic drug pump implant of the present invention designed to deliver sequentially two drugs.

Now referring to FIG. 8, there is provided an osmotic pump implant for providing sustained delivery of two therapeutic agents to a bone, comprising:
   a) a tubular member 61 having a proximal end portion 63, a distal end portion 65 and a throughbore 67,
   b) a semi-permeable membrane 71 located in the proximal end portion of the tubular member,
   c) a distal piston 75 provided in the tubular member, defining an intermediate chamber 77 and a distal chamber 79,
   d) a proximal piston 81 provided in the tubular member, defining the intermediate chamber 77 and a proximal chamber 83,
   e) an osmotic engine 85 located in the proximal chamber,
   f) a first therapeutic drug 91 (for example, a bone forming agent) located in the distal chamber, and
   g) a second therapeutic drug 95 (for example, an anti-resorptive agent) located in the intermediate chamber.

Wherein the tubular member has an outer surface adapted to anchor to the bone, for example, an outer surface having a fastening means 97 (e.g., a threadform) thereon.

In some embodiments, the tubular member has an outer surface which has a hook thereon. In some embodiments, the outer surface has a porosity effective for inducing bone growth, such as a porosity with an average pore size of between about 20 µm and about 500 µm.

The principal mode of action of the device of FIG. 8 is essentially similar to that of FIG. 7, except that two therapeutic agents are sequentially delivered.

In some embodiments, the distal portion of the sidewall of the tubular member has at least one exit hole (see e.g., FIG. 8, and exit hole 99), and the distal piston is sized so that its length is less than the distance from the distal hole and to the sidewall holes. In use, the distal piston travels distally and pushes the BF agent out of each of the distal hole and the sidewall holes. Eventually, the distal piston reaches and seats within the distal end of the chamber. However, since the length of the distal piston is such that it does not occlude the sidewall hole, the AR agent can still elute out of the sidewall holes. Accordingly, the proximal piston pushes the AR agent out of the sidewall holes.

Since the treatment of osteoporosis is benefited by the sequential, continuous administration of the BF agent and the AR agent, this embodiment is advantageous because it allows for the sequential, continuous administration of the BF agent and the AR agent.

Accordingly, in another aspect of the present invention, there is provided a kit for treating osteoporosis, comprising:
- a) a bone anchor comprising:
  - i) an outer surface having at least one exit hole,
  - ii) a distal end portion having at least one entry hole, and
  - iii) a throughbore in fluid communication with the entry and exit holes;
- b) a first formulation comprising an effective amount of a bone forming agent, and
- c) a second formulation comprising an effective amount of an anti-resorptive agent.

Although the device of FIG. 4 is useful for delivering an anti-resorptive agent for a period of at least 6 months, the requirement that the AR agent be delivered ad infinitum requires replacement of the device of FIG. 4 with another device. However, it is believed that replacement of the device of FIG. 4 will be problematic for at least two reasons. First, removal of the device (for example, by turning the threadform in the opposite direction) may well damage the bone surrounding the device. This damage may produce a loose fit between the bone and the second device when it is ultimately inserted into the bone. Second, because the device has administered a bone forming agent and an anti-resorptive agent to the bone, the threadform may have been osteointegrated into the bone, thereby making its removal extremely difficult.

Accordingly, there is a need for a device that allows for easy removal of the drug pump.

Figure 9:
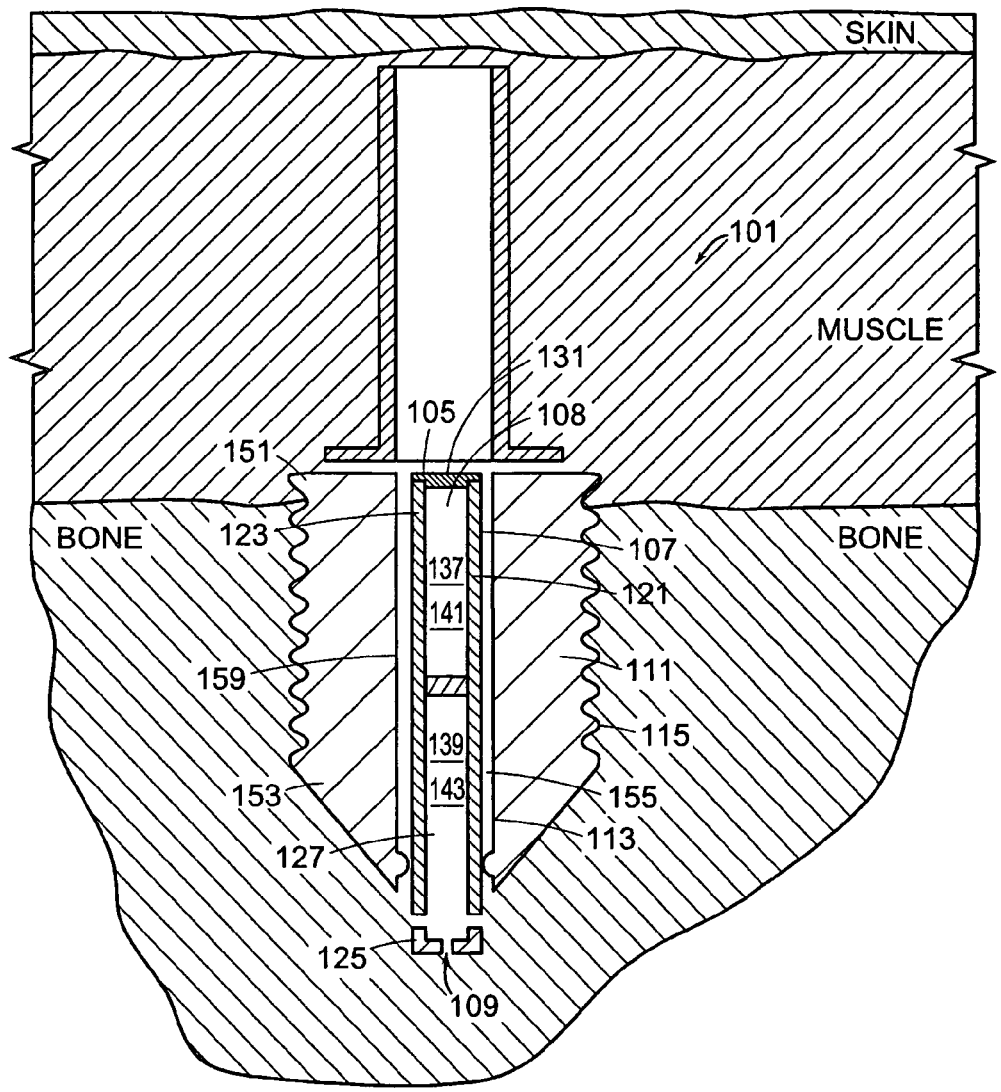
FIG. 9 is a cross-section of a modular drug delivery device of the present invention.

For example, now referring to FIG. 9, there is provided a drug delivery implant 101 for providing sustained delivery of a therapeutic agent to a bone, comprising:
- a) an osmotic pump 105 having an outer surface 107, an inner chamber 108 and an exit port 109, and
- b) a carrier 111 having a recess 113 for receiving the osmotic pump and a means for fastening to bone 115.

The drug delivery implant of the present invention is advantageous because it allows for the intermittent removal and replacement of a spent osmotic pump without harming the surrounding bone.

In some embodiments, the osmotic pump comprises:
- a) a tubular member (i.e., tube) 121 including a proximal end portion 123, a distal end portion 125 and a throughbore 127,
- b) a semi-permeable membrane 131 located in the proximal end portion of the tubular member,
- c) a piston 135 provided in the tubular member, defining a proximal chamber 137 and a distal chamber 139,
- d) an osmotic engine 141 located in the proximal chamber, and
- e) a therapeutic drug 143 located in the distal chamber.

In some embodiments, the carrier 111 comprises a tubular member comprising:
- i) proximal end portion 151,
- ii) a distal end portion 153 and
- iii) a throughbore 155 defining an inner surface 159, wherein the outer surface has a threadform 115 thereon and the inner surface is adapted for releasable engagement of the outer surface of the osmotic pump.

In some embodiments, the implant comprises a throughbore in fluid communication with the exit port. In some embodiments, the drug pump comprises an osmotic engine disposed within the throughbore. In some embodiments, the drug pump contains a formulation (e.g., a first formulation) comprising an effective amount of a bone-forming agent and/ or an anti-resorptive agent. In some embodiments, the drug pump comprises a cylindrical outer surface, the carrier has a throughbore and the cylindrical outer surface is adapted to fit within the throughbore.

In use, the device is implanted into the bone and the first osmotic pump is actuated and provides therapeutic amounts of drug to the patient. After the first osmotic pump is spent, it is removed and replaced by a second fresh osmotic pump. This process can be continued indefinitely.

In some spinal fields, problematic intervertebral discs are often removed and replaced with either a fusion cage or a motion disc. In each case, one benefit of the implant is the restoration of disc height between adjacent vertebrae lost during degeneration of the disc. However, osteoporotic patients who are otherwise candidates for prosthetic disc or fusion cage replacement may be excluded from these surgeries due to concerns that the severity of the osteoporosis may cause the natural endplates adjacent the problematic intervertebral disc to subside into the implant, thereby decreasing the height of the disc space.

Accordingly, in one aspect of the present invention, the device of the present invention is inserted into at least one (and preferably both) of the osteoporotic vertebral bodies adjacent to the intervertebral disc targeted for replacement.

Therefore, in accordance with the present invention, there is provided a method of treating an osteoporotic patient, comprising the steps of:
- a) providing an osteoporotic patient having a functional spinal unit comprising i) an upper vertebral body, ii) a lower vertebral body and iii) an intervertebral disc therebetween,
- b) inserting a device adapted to deliver an effective amount of a bone growth agent into at least one of the vertebral bodies,
- c) removing at least a portion of the intervertebral disc to create a disc space, and
- d) inserting a spinal implant into the disc space.

In some embodiments the device of the present invention is inserted into the adjacent vertebrae prior to the disc replacement surgery. In some embodiments, the insertion of the device of the present invention is inserted into the adjacent vertebrae about one to about twelve months prior to the disc replacement surgery, for example, between about one and about six months, e.g., between about three and about six months.

In one embodiment, the device is adapted to deliver an effective amount of an anti-resorptive agent as well. In one embodiment, the device is adapted to deliver the agent or agents into both of the vertebral bodies.

In some embodiments, the implant is a fusion cage. In others, it is a motion disc. The motion disc is preferably selected from the group consisting of a cushion disc and an articulating disc. In some embodiments, the articulating disc comprises
- a) a first prosthetic vertebral endplate comprising:
  - i) an outer surface adapted to mate with a vertebral body and
  - ii) an inner surface comprising a first articulation surface suitable for supporting articulation motion; and
- b) a second prosthetic vertebral endplate comprising:
  - i) an outer surface adapted to mate with a vertebral body and
  - ii) an inner surface comprising a second articulation surface suitable for supporting articulation motion.

In some embodiments, the motion disc is a two-piece design (wherein the articulation surfaces of the prosthetic endplates are adapted to form an articulation interface). In others, the motion disc is a three-piece design further including a core (wherein opposed articulation surfaces of the core are adapted to form two articulation interfaces with the corresponding articulation surfaces of the prosthetic endplates). Likewise, the implant of the present invention can be implanted into an osteoporotic or osteopenic hip or knee prior to replacement thereof with a prosthetic hip or knee.

In some embodiments, the spent osmotic pump can be removed by a device comprising a magnet.

Figure 10:
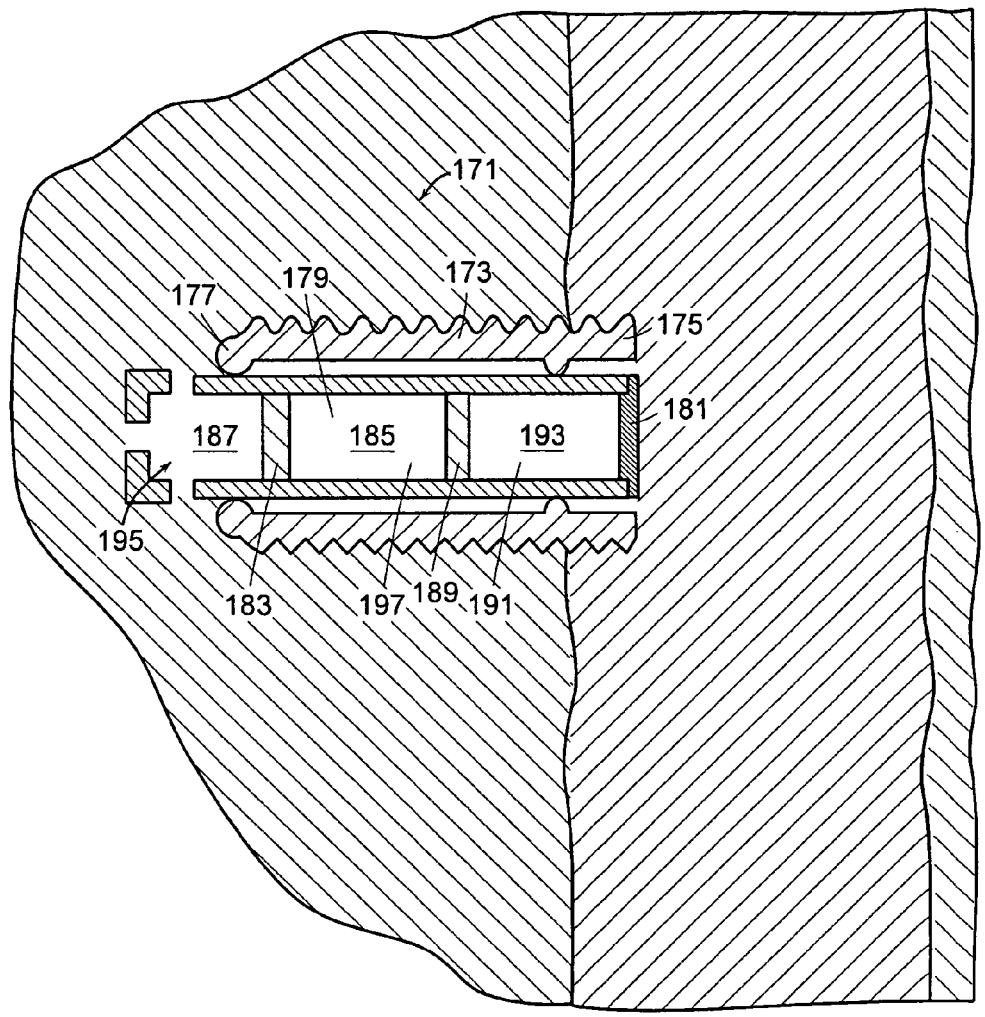
FIG. 10 is a cross-section of a modular drug delivery device of the present invention designed to deliver sequentially two drugs.

In one embodiment (for example, as shown in FIG. 10), there is provided a drug delivery device having both a modular design and a dual drug delivery capability. Accordingly, it has all the advantages of the devices shown in earlier Figures, but with further advantages.

Now referring to FIG. 10, there is provided an osmotic pump implant 171 for providing sustained delivery of at least two therapeutic drugs to a bone, comprising:
- a) a tubular member 173 having a proximal end portion 175, a distal end portion 177 and a throughbore 179,
- b) a semi-permeable membrane 181 located in the proximal end portion of the tubular member,
- c) a distal piston 183 provided in the tubular member, defining an intermediate chamber 185 and a distal chamber 187,
- d) a proximal piston 189 provided in the tubular member, defining the intermediate chamber and a proximal chamber 191,
- e) an osmotic engine 193 located in the proximal chamber, and
- f) a first therapeutic drug 195 (preferably, a bone forming agent) located in the distal chamber,
- g) a second therapeutic drug 197 (preferably, an anti-resorptive agent) located in the intermediate chamber.

In some embodiments, the carrier comprises a tubular member comprising:
- i) a proximal end portion,
- ii) a distal end portion, and
- iii) a throughbore defining an outer surface and an inner surface, wherein the outer surface has a threadform thereon and the inner surface is adapted for releasable engagement of the outer surface of the osmotic pump.

In other embodiments, the formulation is delivered into the bone through the endplate of the vertebral body.

When a modular drug delivery device is selected, the system should be designed so that the drug pump is easily insertable into the carrier, remains in place during use and is easily removable.

Figure 12:
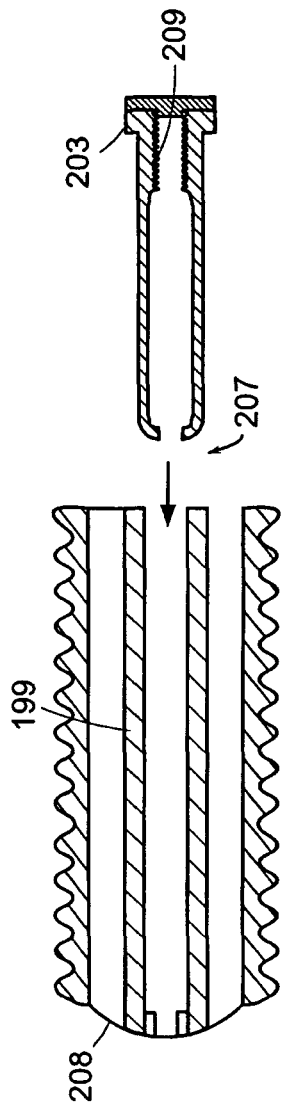
FIG. 12 is a cross-section of another embodiment of a modular drug delivery device of the present invention.
Figure 13:
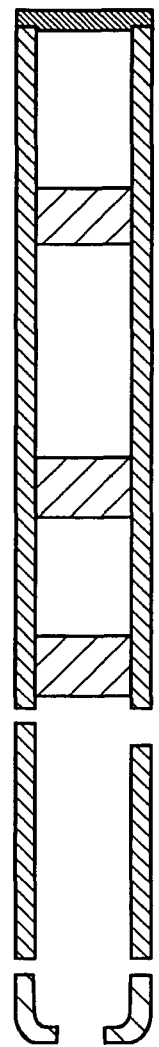
FIG. 13 is a cross-section of an osmotic drug pump of the present invention designed to allow initial administration of a bone forming agent and then co-administration of anti-resorptive and bone forming agents.

In some embodiments (for example, as shown in FIG. 12), these attributes are achieved by providing a rubber annulus 199 upon the inner annulus of the drug pump bore.

When the drug pump must be replaced, the clinician is confronted with the problem of finding the pump (whose proximal end is located a few centimeters below the skin surface) and redamaging soft tissue overlying the pump. Accordingly, in some embodiments, and now referring to FIG. 11, the carrier is provided with a proximal transmuscular tube 200 located proximal to its threaded portion and in fluid communication with the throughbore. Because the tube extends essentially all the way to the skin surface, the clinician will now be able to locate the device with relative ease. In addition, the clinician no longer needs to re-damage the soft tissue lying between the skin and the target bone. In some embodiments, the tube may be perforated with holes 202 for providing fluid access to the semi-permeable membranes of the osmotic pump.

Figure 11:
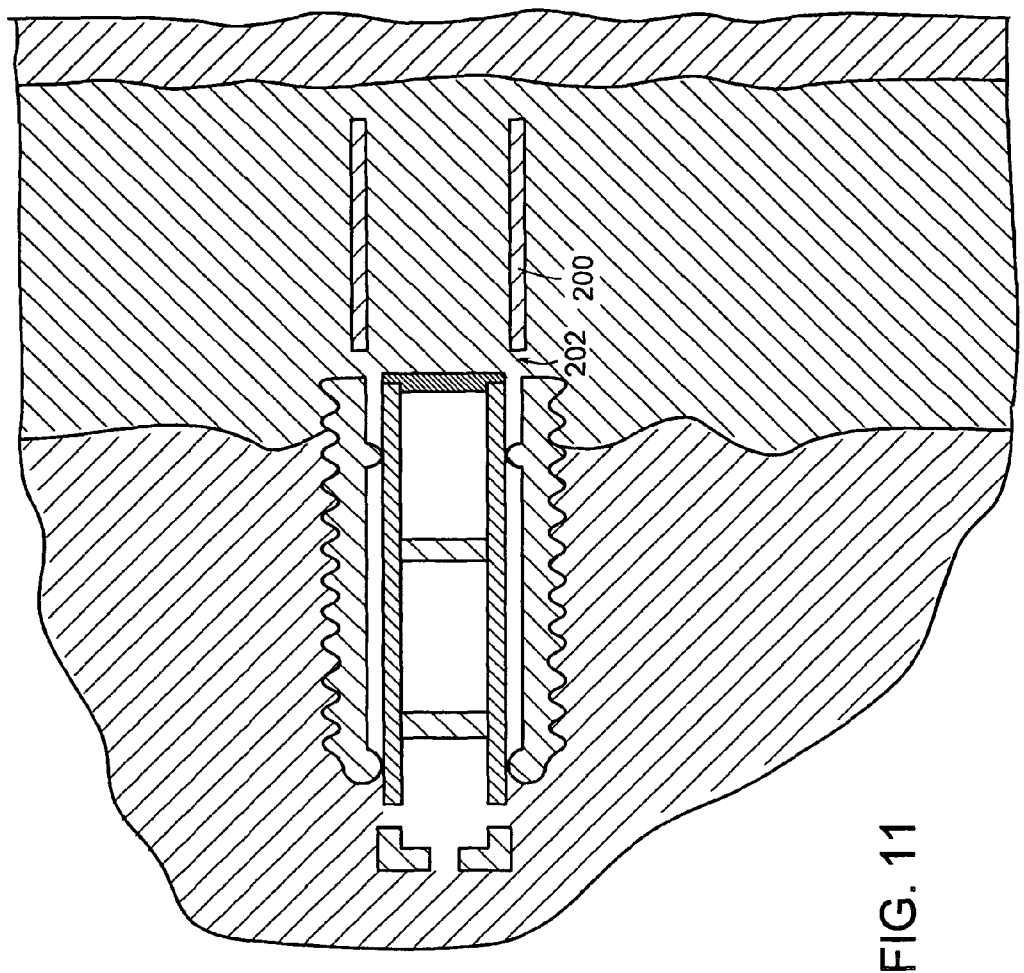
FIG. 11 is a cross-section of a modular drug delivery device of the present invention designed to deliver sequentially two drugs, which is provided with a flexible proximal tube.
Figure 14:
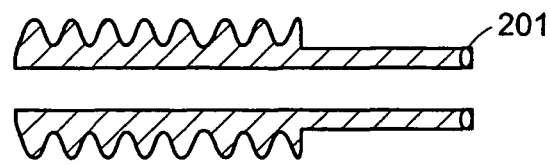
FIG. 14 is a cross-section of a carrier of the present invention having radio-opaque markers.

Now referring to FIG. 11, in some embodiments, the proximal portion of the flexible tube is provided with a radio-opaque marker 201 (See FIG. 14) so that its identification under fluroscopy is even easier. In other embodiments, the radio-opaque marker(s) are replaced with LEDs.

In some patients, the osteoporosis may be so extensive that a threadform-based carrier may not provide a sufficient purchase into the bone, thereby producing implant instability. Accordingly, in some embodiments, the carrier comprises a helix.

Therefore, in accordance with the present invention, a drug delivery implant for providing sustained delivery of a therapeutic agent to a bone is provided, comprising:
- a) an osmotic pump having an outer surface and an exit port, and
- b) a substantially helical carrier defining an inner recess, wherein the osmotic pump is received within the inner recess.

Now referring to FIG. 12, in order to ease the insertion of the drug pump into the carrier and to mitigate any potential rubber wear issues, the distal end of the drug pump may be provided with a beveled nose 207 or bulleted nose. Likewise, the carrier may be provided with a beveled distal end 208 as well.

After the drug pump has dispensed the drug, it should be removed from the patient and replaced with a new one. However, since the pump has been securely situated with the carrier, its removal may be problematic. Accordingly, in some embodiments, the drug pump is provided with removal means. In some embodiments, and still referring to FIG. 12, the removal means comprises a thread 209 provided upon the inner annulus of the drug pump. In some embodiments, the spent osmotic pump can have a removal thread 209 on its inner bore (as shown in FIG. 12), and be removed by a device (not shown) having a complementary thread. During removal, the clinician inserts a screwdriver down the carrier tube and breaches the proximal semi-permeable membrane of the pump, thereby gaining access to the pump bore. The screwdriver is fitted with a thread that mates with the thread located upon the inner surface of the drug pump. Subsequent rotation of the screwdriver engages the pump to the screwdriver. Lastly, the clinician removes the screwdriver and the pump engaged thereto from the patient.

In other embodiments, the removal means can include a recess provided at the distal end portion of the tube (modular hips).

Figure 15:
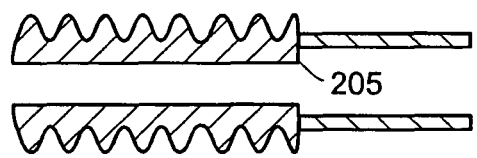
FIG. 15 is a cross-section of a carrier of the present invention having a stop for preventing over-insertion of the drug pump.

Now referring to FIGS. 12 and 15, in some embodiments, the pump has a proximal laterally extending ridge 203, and the carrier has a ledge 205. Together, these features provide a stop that insures the drug pump is not over-extended into the carrier. When a replacement drug pump is provided in the carrier, it would be advantageous to insure the ultimate location of the pump vis-a-vis the carrier. Accordingly, in some embodiments, the drug pump is provided with a stop. In some embodiments, the stop comprises a lip extending radially from the outer surface of the proximal end portion of the pump. When the replacement pump is inserted into the carrier bore, the stop will seat upon a ledge formed upon the proximal end of the annulus, thereby insuring a fixed location within the carrier.

In some embodiments, the barrel of the osmotic pump is made of a titanium alloy.

In some embodiments, the carrier is made of a titanium alloy or carbon-fiber reinforced polymer, such as PEEK. Preferably, it is made of a material having a stiffness relatively close to that of cancellous bone. Preferably, it is made of a material having a stiffness (i.e., a modulus of elasticity) of between about 0.1 and about 10 GPa.

In some embodiments, the exit port holes at the distal end portion of the osmotic pump are coated with a non-stick material, such as TEFLON®. It is believed that the TEFLON® will prevent bony ingrowth into the exit port holes from the bony tissue outside.

In some embodiments, the treatment is delivered by loading a hollowed out fracture fixation device or devices including a tubular bone screw, a tubular lag screw, and a fracture fixation plate. These devices can be either metallic or non-metallic, and absorbable or non-absorbable. As above, these devices may also have two compartments: one loaded with a bone forming agent and a second loaded with an anti-resorptive agent. In another embodiment, one compartment is loaded with the bone forming and anti-resorptive agents contained in bioabsorbable macro-spheres. The macrosphere dissolution is tailored such that the bone forming agents are released first followed by the release of the anti-resorptive agent. In some embodiments, the macro-spheres are constructed such that both drugs are released simultaneously.

Figure 17A:
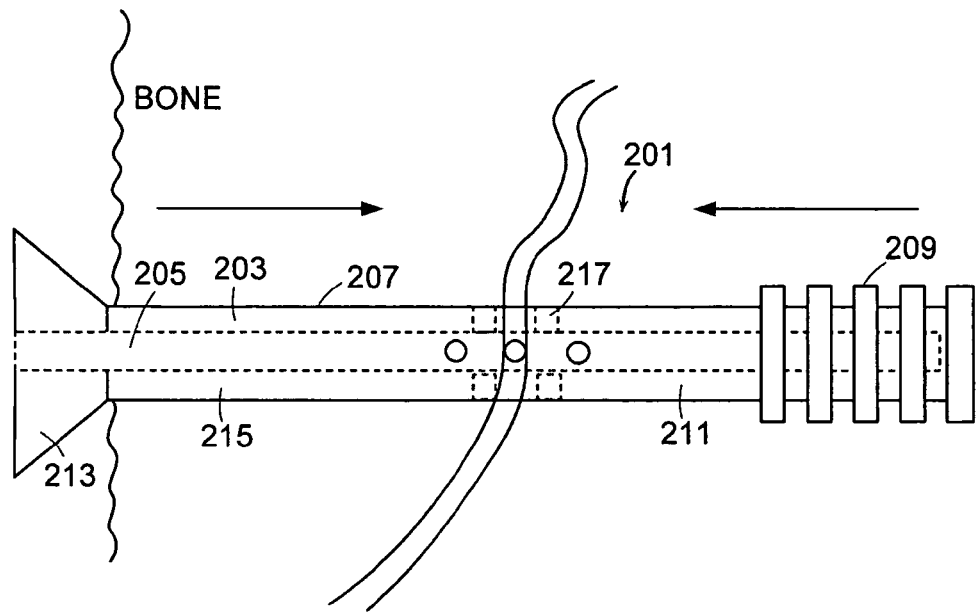
FIGS. 17A-B each disclose a lag screw of the present invention adapted to deliver bone-forming and anti-resorptive agents to a fracture site in bone.

Now referring to FIG. 17a, there is provided a cannulated lag screw adapted to deliver bone-forming and anti-resorptive agents to a fracture site in the bone. The lag screw 201 of the present invention comprises:
  a) a tubular portion 203 containing a bore 205 and an outside surface 207,
  b) a threaded portion 209 located upon a proximal portion 211 of the outside surface,
  c) a plurality of holes 217 connecting the bore and the outside surface, and
  d) a stop 213 located upon a distal portion 215 of the outside surface.

As with conventional lag screws, when the threaded distal portion of the tubular portion is advanced beyond the fracture and the stop begins to abut the bone surface, the lag screw acts as a vise to close the fracture.

In one embodiment, the bore 205 of FIG. 17a is filled with a first plurality of macrospheres containing a bone forming agent (such as MP-52 BMP14), and a second plurality of macrospheres containing an anti-resorptive agent (such as infliximab). MP-52 is described in detail in PCT Publication No. WO 93/16099 (Neidhardt), the entire contents of which are incorporated herein by reference in their entirety. The macrospheres are designed so that the bone-forming agent is released in about the first month, and the anti-resorptive agent is released thereafter.

Figure 17B:
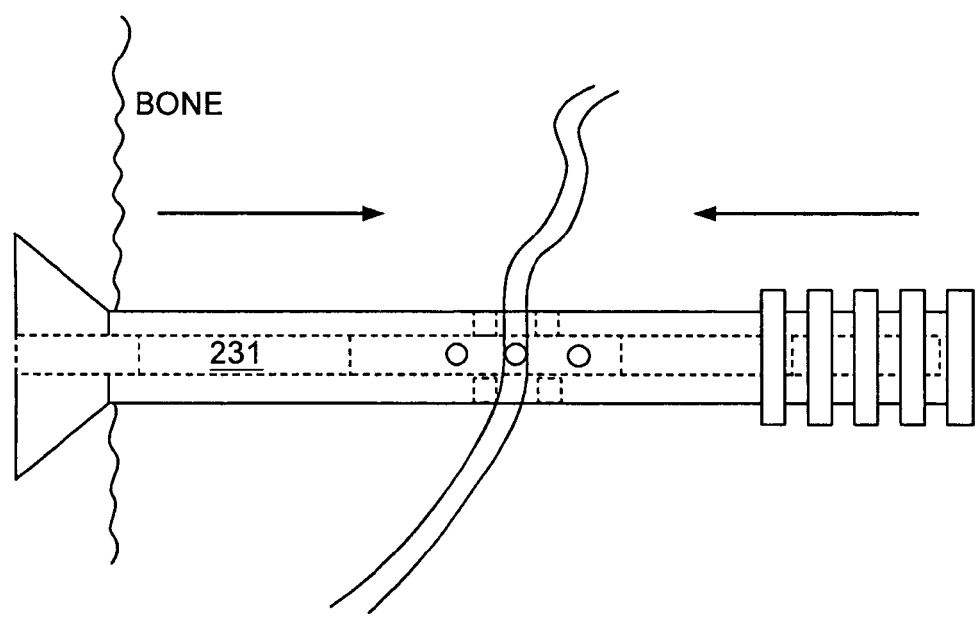

In the embodiment of FIG. 17b, the bore contains an osmotic drug pump 231 containing a bone forming agent (such as MP52), and an anti-resorptive agent (such as infliximab). The pump is designed so that the bone-forming agent is released in about the first month, and the anti-resorptive agent is released thereafter.

Although the devices of the present invention are well suited for treating osteoporosis, these devices may also be used to treat other pathologies, including cancer tumors located in bones. For example, the device of FIG. 7 may be adapted to locally deliver an anti-cancer drug to a tumor located in a bone by simply replacing the anti-resorptive agent with an anti-cancer drug. The dual delivery device of FIG. 8 may be used if the cancer has caused osteoporosis as well. The modular device of FIG. 9 may be used if it is believed the patient may benefit from a long term treatment requiring replacement of a spent device with a new device.

In some embodiments, the distal end of the device is located at or near the tumor. In other embodiments, the distal end of the device is located at or near the region (i.e., volume) formerly occupied by a tumor.

The present inventors believe that OP can be more effectively prevented than treated. Prevention is more likely to be the most-cost effective approach, considering the enormous cost and morbidity of OP related complications. It would be desirable to achieve as high a peak bone density as possible prior to skeletal maturation. This could be accomplished by considering estrogen injections at menopause for high risk patients. These risk factors include small stature, sedentary life style, post-menopausal caucasian women having a life-long history of calcium deficiency. Other factors include genetic factors, alcoholism, and byparathyroidism.

EXEMPLIFICATION

Example 1

This non-limiting prophetic example describes how to intraosseously administer a first formulation comprising a bone-forming agent and a second formulation comprising a HSCA (an anti-resorptive agent) into an uncoupled resorbing bone.

First, a clinician uses a diagnostic test to verify that a bone within a patient is osteoporotic.

Next, the clinician provides a local anesthetic (such as 5 ml lidocaine) to the region dorsal to the vertebral body to reduce subcutaneous pain.

Next, the clinician punctures the skin of the patient dorsal to the OP bone with a relatively large (e.g., 18-19 gauge) needle having a stylet therein, and advances the needle through subcutaneous fat and dorsal sacrolumbar ligament and muscles to the outer edge of the pedicle, and finally punctures the cortical wall of the uncoupled resorbing bone.

Next, the stylet is removed from the needle.

Next, the clinician receives a drug delivery device of FIG. 9, in which an osmotic drug pump having a smaller outer surface is adapted to fit within the larger bore of the carrier. This outer surface of the drug pump is about 4 mm in diameter. The barrel of the drug pump contains first and second formulations of the present invention.

The first formulation contains an effective amount of bFGF (basic fibroblast growth factor), while the second formulation contains REMICADE® infliximab, and has an infliximab concentration of between about 0.4 mg/ml and about 4 mg/ml.

Next, the physician advances the device co-axially through the cannula and screwed into the cortical wall of the bone. Water enters the semi-permeable membrane of the device, eventually causes the expulsion of the first and then the second formulation into the OP bone.

Example II

This non-limiting prophetic example describes how to intraosseously administer a formulation comprising a HSCA (an anti-resorptive agent) and saline into an uncoupled resorbing bone.

First, a clinician uses a diagnostic test to verify that a bone within a patient has high levels of a particular pro-inflammatory cytokine.

Next, the clinician provides a local anesthetic (such as 5 ml lidocaine) to the region dorsal to the vertebral body to reduce subcutaneous pain.

Next, the clinician punctures the skin of the patient dorsal to the bone with a relatively large (e.g., 18-19 gauge) needle having a stylet therein, and advances the needle through subcutaneous fat and dorsal sacrolumbar ligament and muscles to the outer edge of the bone, and finally punctures the cortical wall of the uncoupled resorbing bone.

Next, the stylet is removed from the needle.

Next, the clinician receives a syringe having a smaller gauge needle adapted to fit within the larger gauge needle. This needle is typically a 22 or 24 gauge needle. The barrel of the syringe contains a formulation of the present invention.

The formulation contains REMICADE® infliximab, and has an infliximab concentration of between about 0.4 mg/ml and about 4 mg/ml.

Next, the clinician advances the smaller needle co-axially through the larger needle and past the distal end of the larger needle and past the cortical wall of the bone. The smaller needle is then further advanced into the center of the cancellous portion. Finally, the clinician depresses the plunger of the syringe, thereby injecting between about 0.1 and 1 ml of the formulation into the OP bone.

Example III

This non-limiting prophetic example is substantially similar to that of Example II, except that the formulation comprises a depot-type sustained release device comprising the co-polymer poly-DL-lactide-co-glycolide (PLG). The formulation contains infliximab as the antagonist, and has an infliximab concentration of between about 30 mg/ml and about 60 mg/ml.

Example IV

This non-limiting prophetic example describes how to administer intraosseously a formulation comprising a bone forming agent (BFA) and an anti-resorptive agent (ARA) into an uncoupled resorbing bone.

First, a clinician uses a diagnostic test to verify that a bone within a patient has high levels of a particular pro-inflammatory cytokine.

Next, the clinician provides a local anesthetic (such as 5 ml lidocaine) to the region dorsal to the vertebral body to reduce subcutaneous pain.

Next, the clinician punctures the skin of the patient dorsal to the bone with a relatively large (e.g., 18-19 gauge) needle having a stylet therein, and advances the needle through subcutaneous fat and dorsal sacrolumbar ligament and muscles to the outer edge of the bone, and finally punctures the cortical wall of the uncoupled resorbing bone.

Next, the stylet and needle are advanced about 7 mm, and then removed thereby leaving a tubular recess in the bone.

Figure 16A:
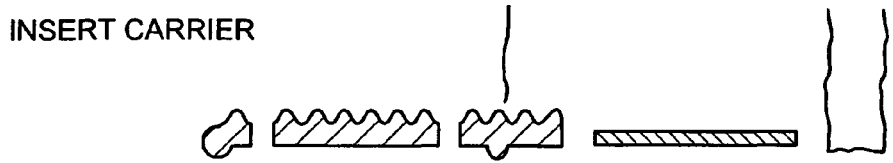
FIGS. 16A-E are cross-sections of a method of using a device of the present invention to treat osteoporotic bone. $BFA_2$: second bone forming agent.

Next, now referring to FIG. 16A, a threaded carrier having an inner throughbore and a plurality of exit holes is inserted into the recess by screwing the thread form into the tubular recess.

Figure 16B:
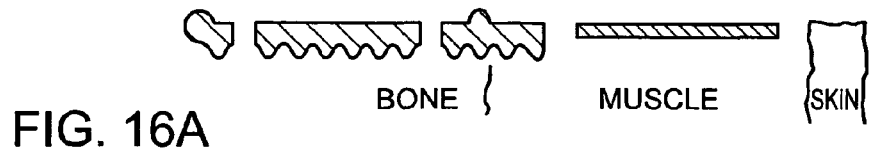

Now referring to FIG. 16B, a cannula is inserted into the throughbore.

Figure 16C:
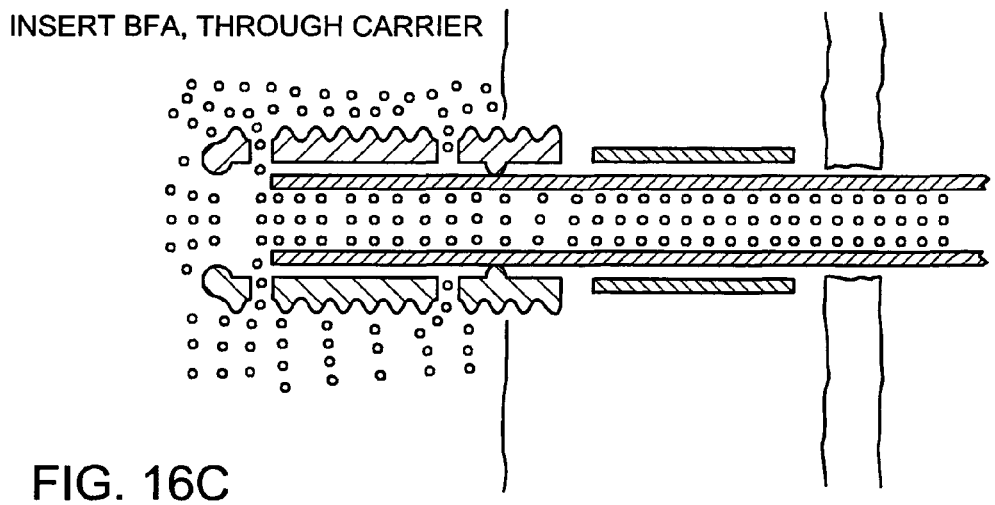
Figure 16D:
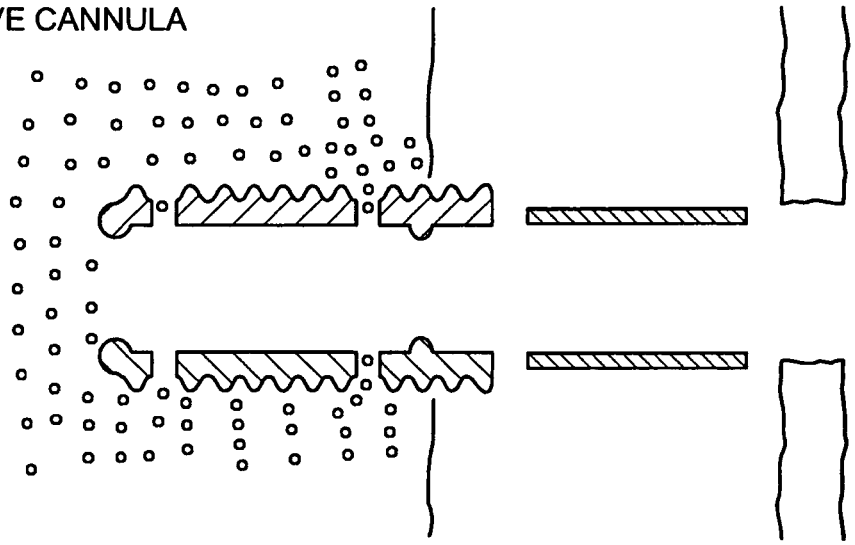

Now referring to FIG. 16C, a flowable particulate bone forming agent (BFA) such as hydroxyapatite is flowed into the proximal end of the cannula. The BFA exits through the exit holes and enters the osteoporotic bone.

Now referring to FIG. 16I), the cannula is removed.

Figure 16E:
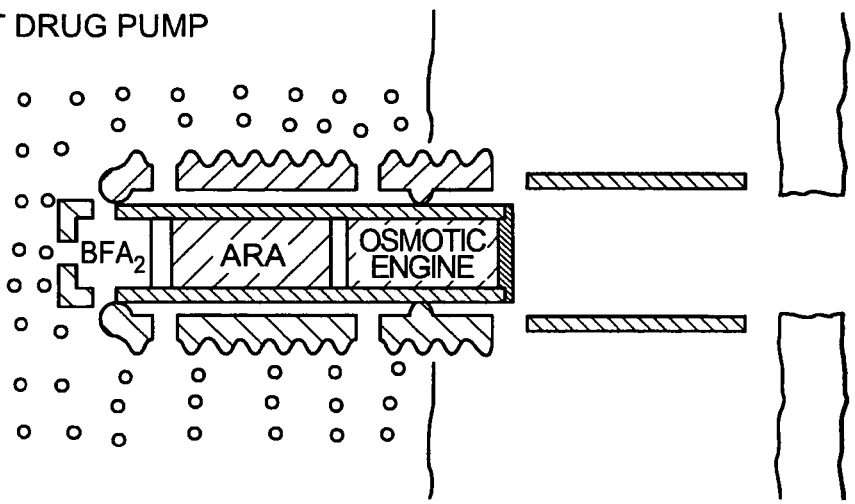

Now referring to FIG. 16E, an osmotic drug pump is snugly placed into the throughbore of the carrier. The drug pump contains a first distally located formulation comprising a second bone forming agent (such as a BMP or FGF) and a second proximally located formulation containing an anti-resorptive agent (ARA) such as REMICADE® infliximab, and has an infliximab concentration of between about 0.4 mg/ml and about 4 mg/ml.

As water infiltrates the semi-permeable membrane of the osmotic pump, the osmotic engine expands thereby, forcing each formulation distally. The first bone forming agent exits through each of the three distal holes. When the distal piston reaches the distal end of the throughbore and blocks the central exit hole, the ARA exits the throughbore through the remaining two lateral holes.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of therapeutically treating an uncoupled resorbing bone in a patient, comprising the steps of:
   a) administering an effective amount of a first formulation comprising a bone forming agent into the cancellous or cortical portion of the uncoupled resorbing bone, and
   b) administering an effective amount of a second formulation comprising an anti-resorptive agent in a sustained release form into the cancellous or cortical portion of the uncoupled resorbing bone, wherein the anti-resorptive agent is a highly specific cytokine antagonist comprising REMICADE® infliximab and wherein an effective amount of the anti-resorptive agent remains within the bone for at least one month after administration of the second formulation.

2. The method of claim 1 wherein the bone is non-fractured.

3. The method of claim 1 wherein the amount of the first formulation comprising the bone forming agent is effective to increase the density of the bone.

4. The method of claim 1 wherein the patient is post-menopausal.

5. The method of claim 1 wherein the uncoupled resorbing bone is a vertebral body.

6. The method of claim 1 wherein the uncoupled resorbing bone is a vertebral body and is adjacent to a fractured vertebral body.

7. The method of claim 1 wherein the uncoupled resorbing bone is a hip bone.

8. A method of treating osteoporosis in a patient, comprising administering an effective amount of a sustained release formulation comprising an effective amount of a highly specific cytokine antagonist into the cancellous or cortical portion of at least one uncoupled resorbing bone, wherein the highly specific cytokine antagonist comprises REMICADE® infliximab and wherein an effective amount of the highly specific cytokine antagonist remains within the bone for at least one month after administration of the formulation.

9. The method of claim 8 wherein at least one bone into which the formulation is administered is non-fractured.

10. The method of claim 8 wherein the amount is effective to increase the bone mineral density of the bone.

11. The method of claim 8 wherein the patient is post-menopausal.

12. The method of claim 8 wherein the bone is a vertebral body.

13. The method of claim 8 wherein the uncoupled resorbing bone is a vertebral body and is adjacent to a fractured vertebral body.

14. The method of claim 8 wherein the bone is osteoporotic.

15. The method of claim 8 wherein the bone is a hip bone.

16. A method of treating an osteoporotic patient having a spinal unit comprising an upper vertebral body, a lower vertebral body, and an intervertebral disc therebetween, comprising: inserting a sustained release device into at least one vertebral body adjacent to the intervertebral disc, wherein the device is adapted to deliver an effective amount of a bone forming agent and an anti-resorptive agent into the cancellous or cortical portion of the vertebral body, and the anti-resorptive agent comprises REMICADE® infliximab and wherein an effective amount of the bone forming agent and anti-resorptive agent remains within the bone for at least one month after administration.

17. A method of therapeutically treating an uncoupled resorbing bone in a patient, comprising administering an effective amount of a sustained release formulation comprising an anti-resorptive agent into the cancellous or cortical portion of the uncoupled resorbing bone, wherein the bone is nontumorous and wherein the anti-resorptive agent is a highly specific cytokine antagonist comprising REMICADE® infliximab and wherein an effective amount of the anti-resorptive agent remains within the bone for at least one month after administration of the formulation.

18. A method of therapeutically treating an uncoupled resorbing bone in a patient, comprising the steps of:
  a) administering an effective amount of a first formulation comprising a bone forming agent into the cancellous or cortical portion of the uncoupled resorbing bone, and
  b) administering an effective amount of a second formulation comprising an anti-resorptive agent in a sustained release form into the cancellous or cortical portion of the uncoupled resorbing bone, wherein the anti-resorptive agent is a highly specific cytokine antagonist comprising REMICADE® infliximab, wherein the second formulation remains in the bone in an effective amount for at least one month.

19. The method of claim 1, wherein the bone forming agent is released from a sustained release device.

20. The method of claim 1, wherein the uncoupled resorbing bone is osteoporotic or osteopenic.

21. The method of claim 8 wherein the anti-resorptive agent remains in the bone in an effective amount for at least two months.

22. The method of claim 16 wherein the device is adapted to deliver the bone forming agent and the anti-resorptive agent into the vertebral body for at least two months.

23. The method of claim 17 wherein the anti-resorptive agent remains in the bone in an effective amount for at least two months.

* * * * *